United States Patent
Consigny et al.

(10) Patent No.: US 9,144,509 B2
(45) Date of Patent: Sep. 29, 2015

(54) METHOD AND APPARATUS FOR DELIVERING AN AGENT TO A KIDNEY

(75) Inventors: Paul M. Consigny, San Jose, CA (US); David C. Gale, Kennesaw, GA (US); Florian Ludwig, Ebikon (CH); Randolpf von Oepen, Los Altos, CA (US); Fozan O. El-Nounou, Santa Clara, CA (US); Pamela A. Kramer-Brown, San Jose, CA (US); Travis R. Yribarren, Coarsegold, CA (US); William E. Webler, Jr., San Jose, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 1218 days.

(21) Appl. No.: 12/902,405

(22) Filed: Oct. 12, 2010

(65) Prior Publication Data
US 2011/0190698 A1    Aug. 4, 2011

Related U.S. Application Data

(63) Continuation-in-part of application No. 11/756,376, filed on May 31, 2007, now Pat. No. 8,216,209.

(51) Int. Cl.
*A61M 31/00* (2006.01)
*A61F 2/958* (2013.01)
*A61M 25/10* (2013.01)

(52) U.S. Cl.
CPC ................ *A61F 2/958* (2013.01); *A61M 25/10* (2013.01)

(58) Field of Classification Search
CPC ..................... A61M 25/04; A61M 2025/0073; A61M 2025/105; A61M 2025/0004; A61M 2025/0681; A61M 2025/1052; A61M 2206/20; A61M 31/002; A61M 25/10
USPC .............. 604/133, 103.01, 27, 93.01, 103.07, 604/131, 509; 623/1.42, 1.2
See application file for complete search history.

(56) References Cited

U.S. PATENT DOCUMENTS

| | | | |
|---|---|---|---|
| 2,701,559 A | 2/1955 | Cooper | |
| 3,105,492 A | 10/1963 | Jeckel | |
| 3,657,744 A | 4/1972 | Ersek | |

(Continued)

FOREIGN PATENT DOCUMENTS

| | | |
|---|---|---|
| DE | 3640745 | 6/1987 |
| DE | 3823060 | 1/1989 |

(Continued)

OTHER PUBLICATIONS

"70th Scientific Assembly and Annual Meeting: Scientific Program", Radiology, Special Edition, vol. 153(P), Washington, D.C., (Nov. 1984), 206.

(Continued)

*Primary Examiner* — Kevin C Sirmons
*Assistant Examiner* — Brandy S Lee
(74) *Attorney, Agent, or Firm* — Randy Shen, Esq.; Blakely Sokoloff Taylor & Zafman LLP

(57) ABSTRACT

Devices for delivering drugs or other treatment agents locally to the vasculature of a mammal are disclosed. These devices have several related structures and are designed to deliver the drugs to facilitate rapid mixing with the blood flowing past the devices.

20 Claims, 9 Drawing Sheets

(56) References Cited

U.S. PATENT DOCUMENTS

| | | |
|---|---|---|
| 3,868,956 A | 3/1975 | Alfidi et al. |
| 3,952,747 A | 4/1976 | Kimmell, Jr. |
| 3,993,078 A | 11/1976 | Bergentz et al. |
| 4,130,904 A | 12/1978 | Whalen |
| 4,140,126 A | 2/1979 | Choudhury |
| 4,159,719 A | 7/1979 | Haerr |
| 4,323,071 A | 4/1982 | Simpson et al. |
| 4,387,952 A | 6/1983 | Slusher |
| 4,503,569 A | 3/1985 | Dotter |
| 4,504,354 A | 3/1985 | George et al. |
| 4,512,338 A | 4/1985 | Balko et al. |
| 4,516,972 A | 5/1985 | Samson |
| 4,531,933 A | 7/1985 | Norton et al. |
| 4,553,545 A | 11/1985 | Maass et al. |
| 4,560,374 A | 12/1985 | Hammerslag |
| 4,580,568 A | 4/1986 | Gianturco |
| 4,616,652 A | 10/1986 | Simpson |
| 4,619,246 A | 10/1986 | Molgaard-Nielsen et al. |
| 4,649,922 A | 3/1987 | Wiktor |
| 4,650,466 A | 3/1987 | Luther |
| 4,655,771 A | 4/1987 | Wallsten |
| 4,665,918 A | 5/1987 | Garza et al. |
| 4,681,110 A | 7/1987 | Wiktor |
| 4,693,243 A | 9/1987 | Buras |
| 4,706,671 A | 11/1987 | Weinrib |
| 4,733,665 A | 3/1988 | Palmaz |
| 4,739,762 A | 4/1988 | Palmaz |
| 4,740,207 A | 4/1988 | Kreamer |
| 4,748,982 A | 6/1988 | Horzewski et al. |
| 4,760,849 A | 8/1988 | Kropf |
| 4,762,128 A | 8/1988 | Rosenbluth |
| 4,767,418 A | 8/1988 | Deininger et al. |
| 4,768,507 A | 9/1988 | Fischell et al. |
| 4,776,337 A | 10/1988 | Palmaz |
| 4,793,348 A | 12/1988 | Palmaz |
| 4,795,458 A | 1/1989 | Regan |
| 4,800,882 A | 1/1989 | Gianturco |
| 4,830,003 A | 5/1989 | Wolff et al. |
| 4,848,343 A | 7/1989 | Wallsten et al. |
| 4,856,516 A | 8/1989 | Hillstead |
| 4,870,966 A | 10/1989 | Dellon et al. |
| 4,877,030 A | 10/1989 | Beck et al. |
| 4,878,906 A | 11/1989 | Lindemann et al. |
| 4,886,062 A | 12/1989 | Wiktor |
| 4,887,997 A | 12/1989 | Okada |
| 4,892,539 A | 1/1990 | Koch |
| 4,893,623 A | 1/1990 | Rosenbluth |
| 4,907,336 A | 3/1990 | Gianturco |
| 4,913,141 A | 4/1990 | Hillstead |
| 4,921,479 A | 5/1990 | Grayzel |
| 4,921,484 A | 5/1990 | Hillstead |
| 4,922,905 A | 5/1990 | Strecker |
| 4,923,464 A | 5/1990 | DiPisa, Jr. |
| 4,943,346 A | 7/1990 | Mattelin |
| 4,950,227 A | 8/1990 | Savin et al. |
| 4,963,022 A | 10/1990 | Sommargren |
| 4,969,458 A | 11/1990 | Wiktor |
| 4,969,890 A | 11/1990 | Sugita et al. |
| 4,986,831 A | 1/1991 | King et al. |
| 4,988,356 A | 1/1991 | Crittenden et al. |
| 4,990,155 A | 2/1991 | Wilkoff |
| 4,994,071 A | 2/1991 | MacGregor |
| 4,998,539 A | 3/1991 | Delsanti |
| 5,002,560 A | 3/1991 | Machold et al. |
| 5,007,926 A | 4/1991 | Derbyshire |
| 5,015,253 A | 5/1991 | MacGregor |
| 5,019,085 A | 5/1991 | Hillstead |
| 5,019,090 A | 5/1991 | Pinchuk |
| 5,026,377 A | 6/1991 | Burton et al. |
| 5,034,001 A | 7/1991 | Garrison et al. |
| 5,035,706 A | 7/1991 | Giantureo et al. |
| 5,037,377 A | 8/1991 | Alonso |
| 5,037,392 A | 8/1991 | Hillstead |
| 5,037,427 A | 8/1991 | Harada et al. |
| 5,053,008 A | 10/1991 | Bajaj |
| 5,059,211 A | 10/1991 | Stack et al. |
| 5,061,273 A | 10/1991 | Yock |
| 5,061,275 A | 10/1991 | Wallsten et al. |
| 5,062,829 A | 11/1991 | Pryor et al. |
| 5,064,435 A | 11/1991 | Porter |
| 5,071,407 A | 12/1991 | Termin et al. |
| 5,073,694 A | 12/1991 | Tessier et al. |
| 5,078,720 A | 1/1992 | Burton et al. |
| 5,078,726 A | 1/1992 | Kreamer |
| 5,078,736 A | 1/1992 | Behl |
| 5,084,065 A | 1/1992 | Weldon et al. |
| 5,089,005 A | 2/1992 | Harada |
| 5,089,006 A | 2/1992 | Stiles |
| 5,092,877 A | 3/1992 | Pinchuk |
| 5,100,429 A | 3/1992 | Sinofsky et al. |
| 5,102,417 A | 4/1992 | Palmaz |
| 5,104,404 A | 4/1992 | Wolff |
| 5,108,416 A | 4/1992 | Ryan et al. |
| 5,108,417 A | 4/1992 | Sawyer |
| 5,116,318 A | 5/1992 | Hillstead |
| 5,116,360 A | 5/1992 | Pinchuk et al. |
| 5,116,365 A | 5/1992 | Hillstead |
| 5,122,154 A | 6/1992 | Rhodes |
| 5,123,917 A | 6/1992 | Lee |
| 5,133,732 A | 7/1992 | Wiktor |
| 5,133,733 A | 7/1992 | Rasmussen et al. |
| 5,135,536 A | 8/1992 | Hillstead |
| 5,158,548 A | 10/1992 | Lau et al. |
| 5,161,547 A | 11/1992 | Tower |
| 5,163,951 A | 11/1992 | Pinchuk et al. |
| 5,163,952 A | 11/1992 | Froix |
| 5,163,958 A | 11/1992 | Pinchuk |
| 5,171,262 A | 12/1992 | MacGregor |
| 5,180,368 A | 1/1993 | Garrison |
| 5,183,085 A | 2/1993 | Timmermans |
| 5,192,297 A | 3/1993 | Hull |
| 5,192,307 A | 3/1993 | Wall |
| 5,192,311 A | 3/1993 | King et al. |
| 5,195,984 A | 3/1993 | Schatz |
| 5,197,978 A | 3/1993 | Hess |
| 5,207,644 A | 5/1993 | Strecker |
| 5,217,482 A | 6/1993 | Keith |
| 5,222,971 A | 6/1993 | Willard et al. |
| 5,226,913 A | 7/1993 | Pinchuk |
| 5,234,456 A | 8/1993 | Silvestrini |
| 5,242,394 A | 9/1993 | Tremulis |
| 5,242,399 A | 9/1993 | Lau et al. |
| 5,242,452 A | 9/1993 | Inoue |
| 5,254,084 A | 10/1993 | Geary |
| 5,256,146 A | 10/1993 | Ensminger et al. |
| 5,279,565 A | 1/1994 | Klein et al. |
| 5,282,823 A | 2/1994 | Schwartz et al. |
| 5,282,824 A | 2/1994 | Gianturco |
| 5,290,295 A | 3/1994 | Querals et al. |
| 5,290,305 A | 3/1994 | Inoue |
| 5,292,331 A | 3/1994 | Boneau |
| 5,304,120 A | 4/1994 | Crandell et al. |
| 5,304,200 A | 4/1994 | Spaulding |
| 5,306,250 A | 4/1994 | March et al. |
| 5,314,444 A | 5/1994 | Gianturco |
| 5,314,472 A | 5/1994 | Fontaine |
| 5,330,500 A | 7/1994 | Song |
| 5,336,178 A | 8/1994 | Kaplan et al. |
| 5,344,426 A | 9/1994 | Lau et al. |
| 5,354,279 A | 10/1994 | Hofling |
| 5,354,308 A | 10/1994 | Simon et al. |
| 5,356,433 A | 10/1994 | Rowland et al. |
| 5,360,401 A | 11/1994 | Turnland et al. |
| 5,368,566 A | 11/1994 | Crocker |
| 5,372,600 A | 12/1994 | Beyar et al. |
| 5,378,239 A | 1/1995 | Termin et al. |
| 5,383,892 A | 1/1995 | Cardon et al. |
| 5,405,378 A | 4/1995 | Strecker |
| 5,415,637 A | 5/1995 | Khosravi |
| 5,419,777 A | 5/1995 | Hofling |
| 5,421,955 A | 6/1995 | Lau et al. |
| 5,423,745 A | 6/1995 | Todd et al. |
| 5,423,885 A | 6/1995 | Williams |
| 5,445,646 A | 8/1995 | Euteneuer et al. |

(56) References Cited

U.S. PATENT DOCUMENTS

| | | | |
|---|---|---|---|
| 5,449,373 A | 9/1995 | Pinchasik et al. | |
| 5,456,667 A | 10/1995 | Ham et al. | |
| 5,456,694 A | 10/1995 | Marin et al. | |
| 5,458,615 A | 10/1995 | Klemm et al. | |
| 5,476,476 A | 12/1995 | Hillstead | |
| 5,484,449 A | 1/1996 | Amundson et al. | |
| 5,507,768 A | 4/1996 | Lau et al. | |
| 5,514,154 A | 5/1996 | Lau et al. | |
| 5,545,132 A | 8/1996 | Fagan et al. | |
| 5,549,626 A | 8/1996 | Miller et al. | |
| 5,571,135 A | 11/1996 | Fraser et al. | |
| 5,603,721 A | 2/1997 | Lau et al. | |
| 5,609,574 A | 3/1997 | Kaplan et al. | |
| 5,611,775 A | 3/1997 | Machold et al. | |
| 5,626,604 A | 5/1997 | Cottone, Jr. | |
| 5,639,274 A | 6/1997 | Fischell et al. | |
| 5,653,690 A | 8/1997 | Booth et al. | |
| 5,653,691 A | 8/1997 | Rupp et al. | |
| 5,653,727 A | 8/1997 | Wiktor | |
| 5,693,029 A | 12/1997 | Leonhardt | |
| 5,713,860 A | 2/1998 | Kaplan et al. | |
| 5,713,863 A | 2/1998 | Vigil et al. | |
| 5,716,396 A | 2/1998 | Williams, Jr. | |
| 5,720,726 A | 2/1998 | Marcadis et al. | |
| 5,733,303 A | 3/1998 | Israel et al. | |
| 5,733,325 A | 3/1998 | Robinson et al. | |
| 5,735,893 A | 4/1998 | Lau et al. | |
| 5,755,781 A | 5/1998 | Jayaraman | |
| 5,769,816 A | 6/1998 | Barbut et al. | |
| 5,782,855 A | 7/1998 | Lau et al. | |
| 5,800,521 A | 9/1998 | Orth | |
| 5,810,871 A | 9/1998 | Tuckey et al. | |
| 5,817,152 A | 10/1998 | Birdsall et al. | |
| 5,830,217 A | 11/1998 | Ryan | |
| 5,836,965 A | 11/1998 | Jendersee et al. | |
| 5,851,210 A | 12/1998 | Torossian | |
| 5,855,563 A * | 1/1999 | Kaplan et al. | 604/509 |
| 5,855,600 A | 1/1999 | Alt | |
| 5,873,852 A | 2/1999 | Vigil et al. | |
| 5,876,374 A | 3/1999 | Alba et al. | |
| 5,882,335 A | 3/1999 | Leone et al. | |
| 5,891,108 A | 4/1999 | Leone et al. | |
| 5,893,852 A | 4/1999 | Morales | |
| 5,902,332 A | 5/1999 | Schatz | |
| 5,904,670 A | 5/1999 | Schreiner | |
| 5,924,997 A | 7/1999 | Campbell | |
| 5,951,599 A | 9/1999 | McCrory | |
| 5,984,964 A | 11/1999 | Roberts et al. | |
| 5,997,468 A | 12/1999 | Wolff et al. | |
| 6,030,413 A | 2/2000 | Lazarus | |
| 6,066,168 A | 5/2000 | Lau et al. | |
| 6,102,904 A | 8/2000 | Vigil et al. | |
| 6,129,754 A | 10/2000 | Kanesaka et al. | |
| 6,146,358 A | 11/2000 | Rowe | |
| 6,190,405 B1 | 2/2001 | Culombo et al. | |
| 6,210,392 B1 | 4/2001 | Vigil et al. | |
| 6,245,026 B1 | 6/2001 | Campbell et al. | |
| 6,273,910 B1 | 8/2001 | Limon | |
| 6,273,913 B1 | 8/2001 | Wright et al. | |
| 6,280,413 B1 | 8/2001 | Clark et al. | |
| 6,280,414 B1 | 8/2001 | Shah et al. | |
| 6,283,947 B1 | 9/2001 | Mirzaee | |
| 6,287,336 B1 | 9/2001 | Globerman et al. | |
| 6,325,826 B1 | 12/2001 | Vardi et al. | |
| 6,334,871 B1 | 1/2002 | Dor et al. | |
| 6,358,247 B1 | 3/2002 | Altman et al. | |
| 6,402,778 B2 | 6/2002 | Wang | |
| 6,440,162 B1 | 8/2002 | Cox et al. | |
| 6,450,971 B1 | 9/2002 | Andrus et al. | |
| 6,451,044 B1 | 9/2002 | Naghavi et al. | |
| 6,482,178 B1 | 11/2002 | Andrews et al. | |
| 6,494,862 B1 | 12/2002 | Ray et al. | |
| 6,577,895 B1 | 6/2003 | Altman | |
| 6,592,569 B2 | 7/2003 | Bigus et al. | |
| 6,602,226 B1 | 8/2003 | Smith et al. | |
| 6,652,579 B1 | 11/2003 | Cox et al. | |
| 6,656,202 B2 | 12/2003 | Papp et al. | |
| 6,663,880 B1 | 12/2003 | Roorda et al. | |
| 6,685,648 B2 | 2/2004 | Flaherty et al. | |
| 6,695,813 B1 | 2/2004 | Boyle et al. | |
| 6,695,830 B2 | 2/2004 | Vigil et al. | |
| 6,733,474 B2 | 5/2004 | Kusleika | |
| 6,905,476 B2 | 6/2005 | Ponzi | |
| 6,997,903 B2 | 2/2006 | Wijay et al. | |
| 7,097,440 B2 | 8/2006 | Papp et al. | |
| 7,217,255 B2 | 5/2007 | Boyle et al. | |
| 7,241,304 B2 | 7/2007 | Boyle et al. | |
| 2001/0000799 A1 | 5/2001 | Wessman et al. | |
| 2001/0007059 A1 | 7/2001 | Mirzaee | |
| 2001/0010014 A1 | 7/2001 | Trozera | |
| 2001/0012951 A1 | 8/2001 | Bates et al. | |
| 2001/0032011 A1 | 10/2001 | Stanford | |
| 2001/0047138 A1 | 11/2001 | Kokate et al. | |
| 2002/0009535 A1 | 1/2002 | Michal et al. | |
| 2002/0062147 A1 | 5/2002 | Yang | |
| 2002/0077564 A1 | 6/2002 | Campbell et al. | |
| 2002/0082515 A1 | 6/2002 | Campbell et al. | |
| 2002/0090388 A1 | 7/2002 | Humes et al. | |
| 2002/0091408 A1 | 7/2002 | Sutton et al. | |
| 2002/0091409 A1 | 7/2002 | Sutton et al. | |
| 2002/0091436 A1 | 7/2002 | Phelps et al. | |
| 2002/0095141 A1 | 7/2002 | Belef et al. | |
| 2002/0099406 A1 | 7/2002 | St. Germain | |
| 2002/0099407 A1 | 7/2002 | Becker et al. | |
| 2002/0103501 A1 | 8/2002 | Diaz et al. | |
| 2002/0107541 A1 | 8/2002 | Vale et al. | |
| 2002/0107561 A1 | 8/2002 | Pinheiro | |
| 2002/0111648 A1 | 8/2002 | Kusleika et al. | |
| 2002/0111659 A1 | 8/2002 | Davis et al. | |
| 2002/0115942 A1 | 8/2002 | Stanford et al. | |
| 2002/0120286 A1 | 8/2002 | DoBrava et al. | |
| 2002/0120287 A1 | 8/2002 | Huter | |
| 2002/0121472 A1 | 9/2002 | Garner et al. | |
| 2002/0123720 A1 | 9/2002 | Kusleika et al. | |
| 2002/0123755 A1 | 9/2002 | Lowe et al. | |
| 2002/0128679 A1 | 9/2002 | Turovskiy et al. | |
| 2002/0128680 A1 | 9/2002 | Pavlovic | |
| 2002/0128681 A1 | 9/2002 | Broome et al. | |
| 2002/0128706 A1 | 9/2002 | Osypka | |
| 2002/0133092 A1 | 9/2002 | Oslund et al. | |
| 2002/0138094 A1 | 9/2002 | Borillo et al. | |
| 2002/0138095 A1 | 9/2002 | Mazzocchi et al. | |
| 2002/0143360 A1 | 10/2002 | Douk et al. | |
| 2002/0143361 A1 | 10/2002 | Douk et al. | |
| 2002/0151927 A1 | 10/2002 | Douk et al. | |
| 2002/0151959 A1 | 10/2002 | Von Oepen | |
| 2002/0156456 A1 | 10/2002 | Fisher | |
| 2002/0156457 A1 | 10/2002 | Fisher | |
| 2002/0161390 A1 | 10/2002 | Mouw | |
| 2002/0161392 A1 | 10/2002 | Dubrul | |
| 2002/0161393 A1 | 10/2002 | Demond et al. | |
| 2002/0161395 A1 | 10/2002 | Douk et al. | |
| 2002/0165574 A1 | 11/2002 | Ressemann et al. | |
| 2002/0165576 A1 | 11/2002 | Boyle et al. | |
| 2002/0169414 A1 | 11/2002 | Kletschka | |
| 2002/0169458 A1 | 11/2002 | Connors, III | |
| 2002/0169472 A1 | 11/2002 | Douk et al. | |
| 2002/0169474 A1 | 11/2002 | Kusleika et al. | |
| 2002/0173815 A1 | 11/2002 | Hogendijk et al. | |
| 2002/0173817 A1 | 11/2002 | Kletschka et al. | |
| 2002/0183763 A1 | 12/2002 | Callol et al. | |
| 2003/0105515 A1 | 6/2003 | Skubitz et al. | |
| 2003/0109824 A1 * | 6/2003 | Anderson et al. | 604/104 |
| 2003/0114921 A1 | 6/2003 | Yoon | |
| 2003/0125802 A1 | 7/2003 | Callol et al. | |
| 2003/0181973 A1 | 9/2003 | Sahota | |
| 2004/0002650 A1 | 1/2004 | Mandrusov et al. | |
| 2004/0024445 A1 | 2/2004 | Dickson | |
| 2004/0044440 A1 | 3/2004 | Takenaka | |
| 2004/0059179 A1 | 3/2004 | Maguire et al. | |
| 2004/0064091 A1 | 4/2004 | Keren et al. | |
| 2004/0064099 A1 | 4/2004 | Chiu | |
| 2004/0086550 A1 | 5/2004 | Roorda et al. | |
| 2004/0093010 A1 | 5/2004 | Gesswein et al. | |

(56) References Cited

U.S. PATENT DOCUMENTS

| | | | |
|---|---|---|---|
| 2004/0102831 A1 | 5/2004 | Murray, III | |
| 2004/0147939 A1 | 7/2004 | Rabkin et al. | |
| 2004/0162516 A1 | 8/2004 | Mandrusov et al. | |
| 2004/0214772 A1 | 10/2004 | Quay et al. | |
| 2004/0230156 A1 | 11/2004 | Schreck et al. | |
| 2004/0267353 A1 | 12/2004 | Gregorich | |
| 2005/0015048 A1 | 1/2005 | Chiu et al. | |
| 2005/0058711 A1* | 3/2005 | Massengale et al. | 424/473 |
| 2005/0070844 A1 | 3/2005 | Chow et al. | |
| 2005/0070991 A1 | 3/2005 | Pienknagura | |
| 2005/0090888 A1 | 4/2005 | Hines et al. | |
| 2005/0240141 A1 | 10/2005 | Aliski et al. | |
| 2005/0240147 A1 | 10/2005 | Makower et al. | |
| 2005/0245882 A1 | 11/2005 | Elkins et al. | |
| 2005/0288632 A1 | 12/2005 | Willard | |
| 2006/0030814 A1 | 2/2006 | Valencia et al. | |
| 2006/0064009 A1 | 3/2006 | Webler et al. | |
| 2006/0079859 A1 | 4/2006 | Elkins et al. | |
| 2006/0106366 A1 | 5/2006 | Wang | |
| 2006/0189960 A1 | 8/2006 | Kesten et al. | |
| 2006/0224234 A1 | 10/2006 | Jayaraman | |
| 2006/0265043 A1 | 11/2006 | Mandrusov et al. | |
| 2007/0067009 A1 | 3/2007 | Gandhi et al. | |
| 2007/0129752 A1 | 6/2007 | Webler et al. | |
| 2007/0213671 A1 | 9/2007 | Hiatt | |
| 2007/0225634 A1 | 9/2007 | Ferren et al. | |
| 2007/0250035 A1 | 10/2007 | El-Nounou et al. | |
| 2007/0258903 A1* | 11/2007 | Kleiner et al. | 424/9.3 |

FOREIGN PATENT DOCUMENTS

| | | |
|---|---|---|
| DE | 19605864 | 8/1996 |
| EP | 0062300 | 10/1982 |
| EP | 0221570 | 5/1987 |
| EP | 0338816 | 10/1989 |
| EP | 0364787 | 4/1990 |
| EP | 0372789 | 6/1990 |
| EP | 0380668 | 8/1990 |
| EP | 0407951 | 1/1991 |
| EP | 0408245 | 1/1991 |
| EP | 0421729 | 4/1991 |
| EP | 0423916 | 4/1991 |
| EP | 0428479 | 5/1991 |
| EP | 0517075 | 12/1992 |
| EP | 0540290 | 5/1993 |
| EP | 0541443 | 5/1993 |
| EP | 807424 | 11/1997 |
| EP | 1588731 | 10/2005 |
| ER | 0361192 | 4/1990 |
| FR | 2677872 | 12/1992 |
| GB | 2070490 | 9/1981 |
| GB | 2135585 | 11/1983 |
| JP | 62-213762 | 9/1987 |
| JP | 62-231657 | 10/1987 |
| JP | 62-235496 | 10/1987 |
| JP | 63-214264 | 9/1988 |
| JP | 01083685 | 3/1989 |
| JP | 1299550 | 12/1989 |
| JP | 2-174859 | 7/1990 |
| JP | 2-255157 | 10/1990 |
| JP | 03009745 | 1/1991 |
| JP | 03009746 | 1/1991 |
| JP | 3-57465 | 3/1991 |
| JP | 3-151983 | 6/1991 |
| JP | 4-25755 | 2/1992 |
| JP | 63-246178 | 10/1998 |
| WO | WO-89/01798 | 3/1989 |
| WO | WO-89/08433 | 9/1989 |
| WO | WO-91/07139 | 5/1991 |
| WO | WO-92/06734 | 4/1992 |
| WO | WO-92/09246 | 6/1992 |
| WO | WO-9640325 | 12/1996 |
| WO | WO-9742998 | 11/1997 |
| WO | WO-99/66970 | 12/1999 |
| WO | WO-0067825 | 11/2000 |
| WO | WO-01/41861 | 6/2001 |
| WO | WO-01/82835 | 11/2001 |
| WO | WO-03/068306 | 8/2003 |

OTHER PUBLICATIONS

"72nd Scientific Assembly and Annual Meeting: RSNA Scientific Program", Radiology, Special Edition, vol. 161(P), Chicago, IL, (Nov. 1986), 40.

"PE Plus Peripheral Balloon Dilation Catheter", C.R. Bard, Inc., USCI Division, (Aug. 1985).

Abbot P4354, "U.S. Appl. No. 10/802,435, filed Mar. 16, 2004".

Abbott Cardiovascular Systems, Final office action dated Jun. 30, 2009 for U.S. Appl. No. 10/802,435.

Abbott Cardiovascular Systems, Non final office action dated Dec. 3, 2009 for U.S. Appl. No. 10/802,435.

Abbott Cardiovascular Systems, International Preliminary Report on Patentability dated Dec. 10, 2009 for PCT/US2008/005947.

Abbott Cardiovascular Systems, Non final office action dated Feb. 24, 2010 for U.S. Appl. No. 11/756,376.

Abbott Cardiovascular Systems, Final office action dated Jun. 2, 2010 for U.S. Appl. No. 10/802,435.

Abbott Cardiovascular Systems, Final Office Action mailed Nov. 22, 2010 for U.S. Appl. No. 11/756,376.

Abbott Cardiovascular Systems, Non-final Office Action mailed May 24, 2011 for U.S. Appl. No. 11/756,376.

Abbott Cardiovascular Systems, Non final office action mailed Aug. 10, 2012 for U.S. Appl. No. 13/446,761.

Abbott Cardiovascular Systems, Non-Final Office Action Dated Oct. 10, 2012 for U.S. Appl. No. 13/158,757.

Abbott Cardiovascular Systems, Inc., "PCT Invitation to Pay Additional Fees and Partial Search Report mailed Aug. 27, 2008", PCT Application No. PCT/US2008/005947, 9 pages.

Abbott Cardiovascular Systems, Inc., "PCT Search Report and Written Opinion mailed Nov. 20, 2008", PCT Application No. PCT/US2008/005947, 26 pages.

Bonzel, T., et al., "The Sliding Rail System (Monorail): Description of a New Technique for Intravascular Instrumentation and Its Application to Coronary Angioplasty", Kardiologie, Supplemental 6, (1987), 119-122.

Charnsangavej, D., et al., "Endovascular Stent for Use in Aortic Dissection: an in Vitro Experiment", Radiology, vol. 157, No. 2, (Nov. 1985), 323-324.

Charnsangavej, Chusilp, et al., "Stenosis of the Vena Cava: Preliminary Assessment of Treatment with Expandable Metallic Stents", Radiology, vol. 161, (Nov. 1986), 295-298.

Cragg, et al., "Non-Surgical Placement of Arterial Endoprostheses: A New Technique Using Nitinol Wire", Radiology Journal, (Apr. 1983), 261-263.

Dotter, Charles T., "Transluminal Expandable Nitinol Coil Stent Grafting: Preliminary Report", Radiology Journal, (Apr. 1983), 259-260.

Dotter, Charles T., "Transluminally Placed Coilspring Endarterial Tube Grafts", Investigative Radiology, (Sep./Oct. 1969), 329-332.

Duprat, et al., "Flexible Balloon-Expanded Stent for Small Vessels", Radiology Journal, (1985), 73-77.

Finci, Leo, et al., "Percutaneous Transluminal Coronary Angioplasty of a Bifurcation Narrowing Using the Kssing Wire Monorail Balloon Technique", The American Journal of Cardiology, vol. 60, (Aug. 1987), 375-376.

Furui, Shigeru, et al., "Hepatic Inferior Vena Cava Obstruction: Treatment of Two Types with Gianturco Expandable Metallic Stents", Radiology, (Sep. 1990), 665-670.

Garasic, Joseph M., et al., "Stent and Artery Geometry Determine Intimal Thickening Independent of Arterial Injury", Circulation, (Feb. 2000), 812-818.

Harrington, J.D., et al., "The Palmaz-Schatz Stent", Handbook of Cardiovascular Interventions/Vascular Interventions, 563-572.

Kaltenbach, M., et al., "Zeitschrift fur Kardiologie", Abstracts, German Journal of Cardiology, Band 80, Supplementum 3, (Apr. 1991), 28-29.

(56) References Cited

OTHER PUBLICATIONS

Lawrence, David D., Jr., et al., "Percutaneous Endovascular Graft: Experimental Evaluation", Radiology, vol. 163, (May 1987), 357-360.
Maass, et al., "Radiological Follow-Up of Transluminally Inserted Vascular Endoprosthese: An Experimental Study Using Expanding Spirals", Radiology Journal, (1984), 659-663.
Mirich, et al., "Percutaneously Placed Endovascular Grafts for Aoertic Aneurysms: Feasibility Study", Radiology, Part 2, (1989), 1033-1037.
Palmaz, et al., "Expandable Intraluminal Graft: A Preliminary Study", Raiodiology Journal, (1985), 73-77.
PCT Search Report, "PCT/US2007/009418", (Oct. 4, 2007).
Rosch, Josef, et al., "Experimental Intrahepatic Portacaval Anastomosis: Use of Expandable Gianturco Stents", Radiology, vol. 162, (Feb. 1987), 481-485.
Rosch, Josef, et al., "Gianturco Expandable Stents in Experimental and Clinical Use", Twelfth Annual Course of Diagnostic Angiography and Interventional Radiology (Pittsburgh, PA), (Mar. 1987), 121-124.
Rosch, Josef, et al., "Gianturco Expandable Wire Stents in the Treatment of Superior Vena Cava Syndrome Recurring after Maximum-Tolerance Radiation", Cancer, vol. 60, (Sep. 1987), 1243-1246.
Rosch, Josef, et al., "Modified Gianturco Expandable Wire Stents in Experimental and Clinical Use", Annales de Radiologie, vol. 31, No. 2, (1988), 100-103.
Rosch, Jr., M.D., et al., "Transjugular Intrahepatic Portacaval Shunt: An Experimental Work", The American Journal of Surgery, vol. 121, (May 1971), 588-592.
Strupp, G., et al., "Clinical and Angiographic Short and Medium Term Results after Coronary Stenting", Zeitschrift fur Kardiologie, vol. 81, (1992), 500-506.
Van Der Geissen, Willem J., et al., "Coronary Stenting with a new, Radiopaque Balloon-Expandable Endoprosthesis in Pigs", Circulation, vol. 83, No. 5, (May 1991), 93-149.
Wallace, Michael J., et al., "Tracheobronchia Tree: Expandable Metallic Stents Used in Experimental and Clinical Applications (Work in Progress)", Radiology, vol. 158, (Feb. 1986), 309-312.
Wright, et al., "Percutaneous Endovascular Stents: An Experimental Evaluation", Radiology Journal, (1985), 69-72.
Yoshioka, et al., "Development and Clinical Application of Biliary Endoprosthesis Using Expandable Metallic Stents", Japan Radiological Society, vol. 48, No. 9, (1988), 1183-1185.
Yoshioka, et al., "Self-Expanding Endovascular Graft: An Experimental Study in Dogs", American Journal of Roentgeriology, vol. 151, (Oct. 1988), 673-676.
Zeltinger, J., et al., "Advances in the Development of Coronary Stents", Biomaterials Forum, (2004), pp. 8-9, 24.
Abbott Cardiovascular Systems, et al., Final Office Action dated Mar. 28, 2013 for U.S. Appl. No. 13/446,761.
Abbott Cardiovascular Systems, et al., Final Office Action dated Mar. 27, 2013 for U.S. Appl. No. 13/158,757.
Abbott Cardiovascular Systems, Non-Final Office Action mailed Oct. 21, 2013 for U.S. Appl. No. 13/158,757.
Abbott Cardiovascular Systems, Final Office Action mailed May 23, 2014, U.S. Appl. No. 13/158,757.
Abbott Cardiovascular Systems, Final Office Action mailed Jun. 5, 2014 for U.S. Appl. No. 13/446,768.
Abbott Cardiovascular Systems, Non-Final Office Action mailed Nov. 14, 2014 for U.S. Appl. No. 13/158,757.
Abbott Cardiovascular Systems, First Action Interview Pilot Program Pre-Interview Communication mailed Dec. 3, 2014, U.S. Appl. No. 13/154,258.
Non-Final Office Action mailed Jan. 13, 2015 for U.S. Appl. No. 13/446,768.

* cited by examiner

METHOD AND APPARATUS FOR DELIVERING AN AGENT TO A KIDNEY

REFERENCE TO RELATED APPLICATIONS

This application is a Continuation-in-Part of U.S. patent application Ser. No. 11/756,376; entitled: "Method and Apparatus for Delivering an Agent to a Kidney"; filed on May 31, 2007, the entire disclosure of with is hereby incorporated by reference.

BACKGROUND

Many diseases that affect organs develop over a decade or more. During this time, the function of the organ diminishes. The end-stage of many of these diseases is a transplant or some other treatment to supply artificially the organ's function—dialysis in the case of kidney disease such as end-stage renal disease, for example. A number of factors including immune system disorders or diabetes can cause these types of diseases.

Different diseases call for different treatments depending upon the dysfunction of the organ. For many of these diseases, the standard for treatment, short of a transplant, is drug-based. Drug-based treatments are usually systemic and typically use a pill or infusion of a solution of the drug in a carrier. These delivery methods are systemic because the patient's whole system is treated. But systemic treatment requires supplying the whole system drugs at levels high enough to be effective at the target organ. Achieving effective levels at the target organ frequently requires delivering toxic levels throughout the remainder of the system.

On the other hand, locally delivering the drug can alleviate some of the problems with systemic treatment. For instance, local delivery side-steps supplying the drug system-wide allowing for effective local drug levels while maintaining much lower system-wide levels, which are frequently benign to the patient.

But local delivery presents its own set of challenges. Typically, with local delivery, the drug enters the bloodstream upstream of the desired treatment site. Another technique involves injecting the drug into a (temporarily) unperfused region of the vasculature near or in the diseased organ. This technique can use an occlusion device upstream of the delivery region to inhibit or stop blood flow. In either case, the natural laminar flow of blood does not always promote effective mixing between the drug and blood.

Ineffective mixing can prevent the drug from evenly reaching its target organ or region's cells. For example, delivery upstream of an arterial branch coupled with ineffective mixing can result in more drug being delivered down one branch than another.

What is needed is a delivery technique for local delivery that provides effective mixing between the blood and the drug. This need is especially acute for delivery to the kidney because the kidney contains a highly branched arterial vasculature.

SUMMARY

In accordance with an embodiment of this invention, a device comprising a catheter with a main body, an expandable diffusion member, and a drug delivery lumen is disclosed. The expandable diffusion member comprises a body in some embodiments. In these or other embodiments, the body comprises a preformed shape memory material such as nitinol materials, Copper-based materials, or polymeric materials.

In these or other embodiments, the expandable diffusion member comprises a net-like, braided structure. In some of these embodiments, the net-like braided structure comprises one, two, or more wires or filaments. In other embodiments, the expandable diffusion member comprises a toric or donut structure.

In some embodiments the donut structure comprises a substantially cylindrical body with a length, a largest diameter, and a passage coaxial or substantially coaxial to the cylindrical axis. In other embodiments, the passage penetrates the structure in a direction similar to that of the cylindrical axis, but not necessarily coaxial to that axis. In some embodiments comprising the donut structure, the length ranges from 1 to 10 times the largest diameter of the body. In some of these embodiments, the body has a diameter that ranges from 50 to 105% of the vessel diameter. In some of these embodiments, the passage has a diameter that ranges from 15 to 80% of the largest diameter of the cylinder. Some examples of embodiments that comprise the donut structure further comprise a connecting member that joins the main body to the expandable diffusion member.

In some embodiments of the device, the body of the expandable diffusion members comprises a ball of wire or a ball of filament. In some of these embodiments, the wire or filament is formed into a set of co-planer, serpentine curves. Some subsets of these embodiments comprise two or more sets of co-planer curves that can be situated in different planes and that can be substantially parallel to each other.

In some embodiments of the device, the expandable diffusion member further comprises an occlusion balloon.

BRIEF DESCRIPTION OF THE DRAWINGS

The features, aspects, and advantages of the invention will become more apparent from the following detailed description, appended claims, and accompanying drawings.

DETAILED DESCRIPTION

The following description of several embodiments describes non-limiting examples that further illustrate the invention. All titles of sections contained in this document, including those appearing above, are not to be construed as limitations on the invention, but rather they are provided to structure the illustrative description of the invention that is provided by the specification.

Unless defined otherwise, all technical and scientific terms used in this document have the same meanings as commonly understood by one skilled in the art to which the disclosed invention pertains. The singular forms "a", "an", and "the" include plural referents unless the context clearly indicates otherwise. Thus, for example, reference to "fluid" refers to one or more fluids, such as two or more fluids, three or more fluids, etc.

For purposes of this document, the portion of a delivery device designed to create turbulence in the blood flow is called a diffusion member or an expandable diffusion member.

Figure 1:
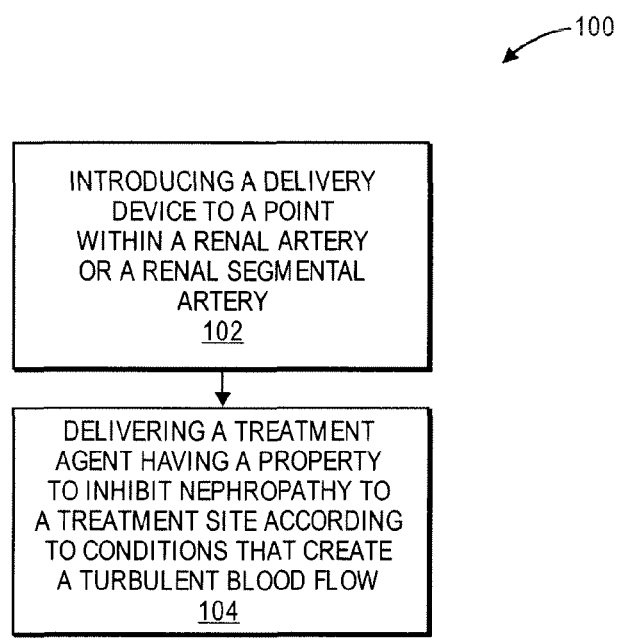
FIG. 1 illustrates a flow chart of a method for delivering a treatment agent to an organ or region.

FIG. 1 shows a flow chart of a method for delivering a treatment agent to a kidney. In one embodiment, the method includes introducing a delivery device to a point within a renal artery or a renal segmental artery that supplies the renal cortex (block 102). Alternatively, the point may be within the renal cortex. The delivery device broadly includes any medical device for insertion into a physiological lumen to permit injection or withdrawal of fluids of varying viscosities to maintain patency of a blood vessel lumen or an area defining the lumen, or for other purposes. The delivery device may further include any medical device capable of releasing a treatment agent after insertion into a physiological lumen. The point at which the delivery device is introduced may be a treatment site or a region adjacent to a treatment site. The treatment site may be a diseased region within a renal vessel or other tissue of a kidney or other organ.

In one embodiment, the treatment agent is delivered according to conditions that create turbulent blood flow within a vessel region where the treatment agent is delivered (block 104). The term "turbulent blood flow" as used in this document generally refers to a flow profile characterized by a chaotic or agitated blood flow or otherwise modified flow profile that may include rapid variations of pressure, flow direction or velocity. For example, in some embodiments, turbulent blood flow arises from partially occluding the vessel lumen by about 60% to about 95%.

Typically, the flow profile of blood flowing through the renal artery to the kidney is laminar, meaning the fluid flows in parallel layers, or streams, with little or no disruption between the layers. This profile continues along the kidney opening, or Ilium, and into the segmental arteries leading to the glomerular capillaries within the renal cortex. Thus, when the delivery device releases the treatment agent from a single point into one of these streams of a healthy kidney, blood flow carries most of the treatment agent only to the kidney region at the end of the stream. In this respect, only a small portion of the kidney receives the treatment agent.

Moreover, blood flow to diseased regions especially in need of the treatment agent may be reduced or stopped altogether because of the disease. In such cases, even where the treatment agent is released into a path normally destined for the diseased region, it will not reach that region. Delivery may overcome such problems by creating turbulence within the flow profile followed by treatment agent delivery into the turbulent blood flow. In particular, these types of turbulent conditions will facilitate mixing of the treatment agent with the blood and disrupt the pathways typically found within the kidney so that the treatment agent is more evenly distributed throughout the kidney.

In one aspect, conditions creating turbulent blood flow may include partially occluding a region of the artery lumen so as to provide a constricted pathway for blood flow (e.g., about 1% to 99%, about 25% to 98%, or about 60% to about 95% lumen occlusion). The narrowed pathway causes the speed of the blood flowing through the narrower region to increase resulting in turbulent blood flow. The treatment agent may then be injected into the turbulent blood flow. Turbulent blood flow may further be created within a lumen of a delivery device. In this aspect, a fluid, such as saline or blood, may be delivered through the lumen of the device and a treatment agent may be injected into the flowing fluid. In other embodiments, the conditions creating a turbulent blood flow may include injecting a treatment agent within a vessel lumen in a direction perpendicular to the direction of blood flow. In this aspect, the stream of treatment agent alters the normal direction of blood flow, bisecting the normal flow path causing turbulence. This turbulence homogeneously distributes the treatment agent throughout the blood for delivery to the treatment site. In addition, this turbulence may disrupt the downstream laminar flow profiles within the kidney. The homogenous distribution of the treatment agent throughout blood flowing to the kidney and disruption of flow profiles within the kidney facilitates a substantially uniform distribution of the treatment agent solution throughout the kidney tissues.

Preventing backflow of the treatment agent further maximizes delivery of the treatment agent to the treatment site. The term "backflow" as used in this document generally refers to a flow of treatment agent in a direction opposite that of the desired delivery direction. For example, in some cases the treatment site is unable to retain the full volume of delivered treatment agent. In this aspect, the excess treatment agent flows back up the vessel. And where delivery is within the renal artery, the excess flows into the adjacent aorta (i.e. backflows). In one embodiment, partially or fully occluding a vessel region upstream from the treatment site before delivering the treatment agent prevents such backflow. Blocking may be accomplished, by expanding, for example, a balloon or a sheath of the delivery device within the vessel. The balloon or sheath substantially backstops any unabsorbed treatment agent delivered to the treatment site diminishing any flow toward the balloon or sheath. Alternatively, releasing the treatment agent from a delivery port of the delivery device at a flow rate less than a natural flow rate of the artery may prevent backflow. For example, the flow rate of blood through the renal artery to the kidney is about 500 milliliters per minute (ml/min). Thus, treatment agent delivery to the renal artery at a flow rate less than about 500 ml/min may prevent backflow.

Figure 2:
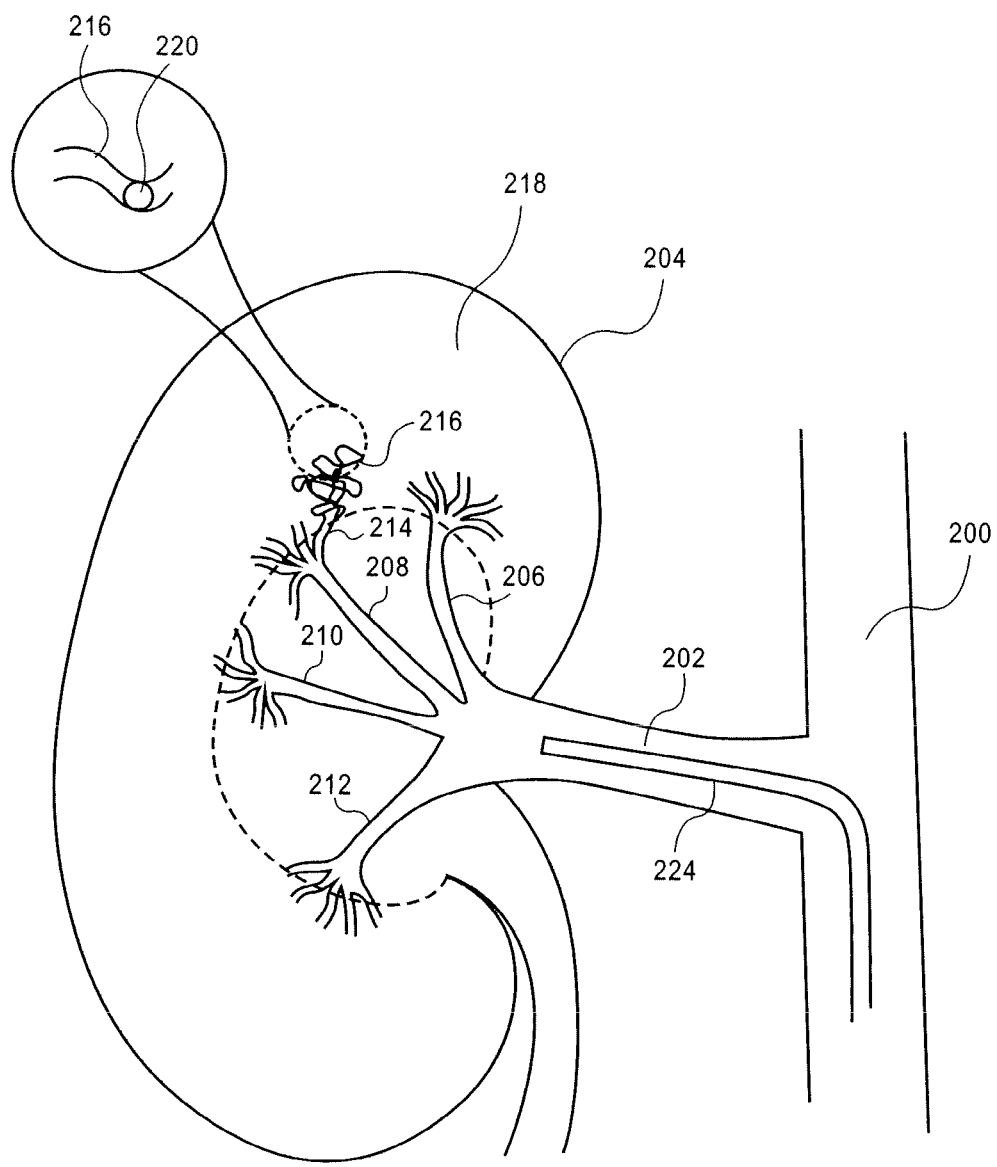
FIG. 2 shows a cross-sectional side view of a kidney and a method for delivering a treatment agent to the kidney.

In other embodiments, altering the particle size of the treatment agent may maximize delivery of an effective amount of the treatment agent to the treatment site. As illustrated in FIG. 2, a lower branch of aorta 200 feeds blood to kidney 204 through renal artery 202. Renal artery 202 branches into renal segmental arteries 206, 208, 210, and 212 and arterioles 214. Each arteriole 214 in turn leads to a tuft of capillaries 216: a glomerulus. Blood from segmental arteries 206, 208, 210 and 212 flows into the glomerulus at the end of each segmental artery 206, 208, 210, and 212 where the blood is filtered to remove fluid and solutes. In one embodiment, as illustrated in FIG. 2, a distal end of delivery device 224 may be positioned at a point within renal artery 202. Alternatively, one may position the delivery device 224 at a point within renal segmental arteries 206, 208, 210, and 212. A proximal portion of delivery device 224 remains outside of the body to facilitate loading of the treatment agent within delivery device 224.

Representatively, a femoral artery may be punctured and delivery device 224 may be advanced through the femoral artery, to aorta 200 and then into renal artery 202. Alternatively, one may advance the delivery device 224 through a brachial artery, down aorta 200 and into renal artery 202. In still further embodiments, an external iliac artery may be punctured and delivery device 224 may be advanced through the external iliac artery to a common iliac artery, to aorta 200 and then into renal artery 202.

It is further contemplated that delivery device 224 may be introduced to a point within kidney 204 using retroperitoneal insertion. In this aspect, a distal end of delivery device 224 may be inserted through a back of a patient adjacent kidney 204. Delivery device 224 may then be advanced through a surface of kidney 204 to a point within renal cortex 218 adjacent to glomerulus 216. In this aspect, when the treatment agent is delivered with delivery device 224, it localizes within an area proximal to glomerular capillaries within the kidney. Alternatively, delivery device 224 may be introduced through a back region of the patient and into renal artery 202. In this embodiment, the treatment agent may then be delivered by delivery device 224 through renal artery 202 to a desired treatment site.

In an embodiment illustrated in FIG. 2, a treatment agent loaded within delivery device 224 may be released into, for example, renal artery 202 such that the treatment agent flows through segmental artery 208 and into glomerulus 216. In one embodiment, the treatment agent may be loaded into a carrier having a large enough diameter such that the carrier lodges within a narrow lumen of a capillary within the glomerulus 216. The exploded view of glomerulus 216 of FIG. 2 shows this aspect. In this embodiment, treatment agent 220 flows into glomerulus 216 and lodges within the lumen. For example, in some embodiments the treatment agent may have a diameter from about 8 microns to about 15 microns. Thus, release of the treatment agent from within the carrier localizes it at glomerulus 216, and the treatment agent remains at a specific treatment site within the kidney.

Useful treatment agents will be discussed below after discussing several embodiments of delivery devices according to embodiments of the invention.

Figure 3:
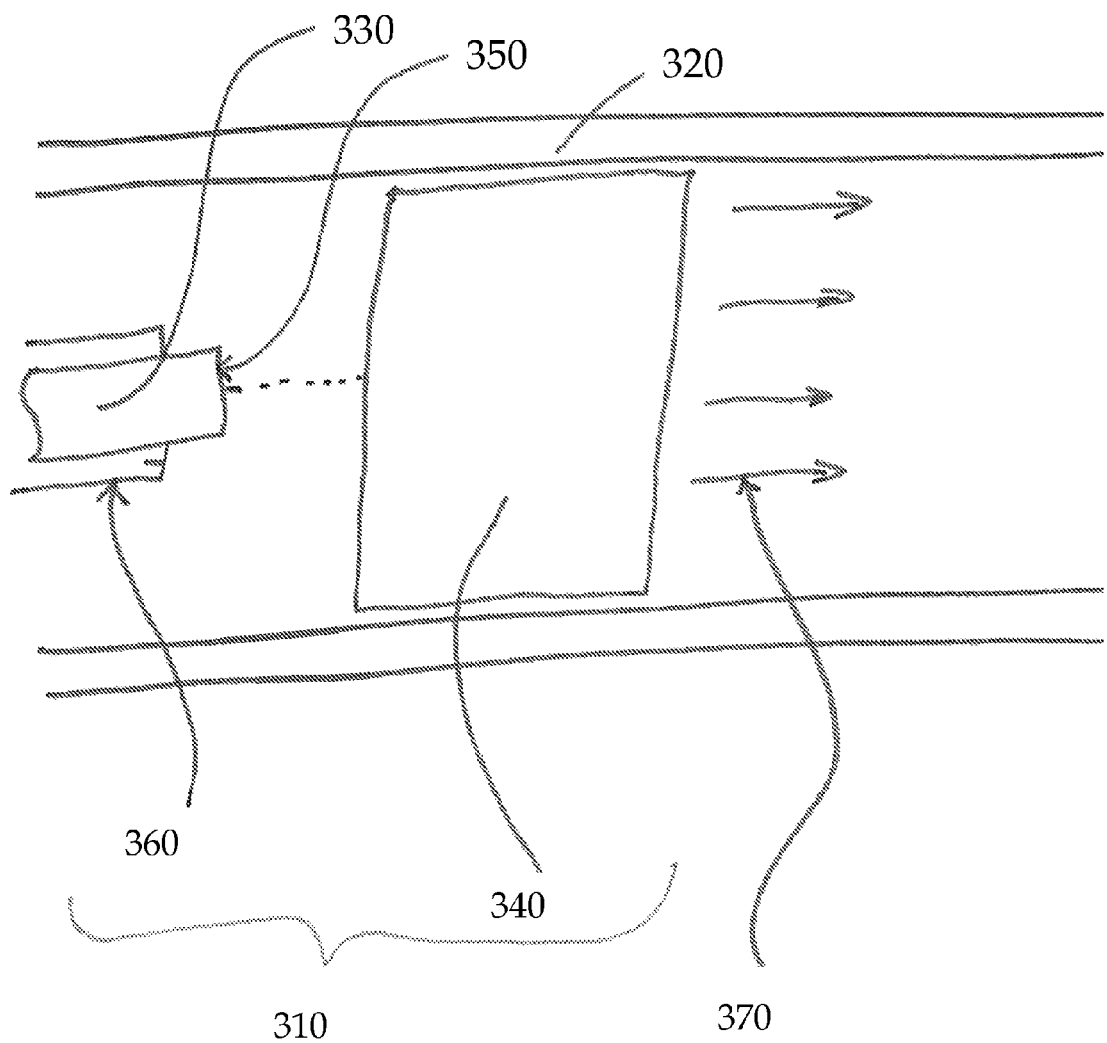
FIG. 3 is a schematic view of a catheter and an expandable diffusion member.

Referring to FIG. 3, the device 310 sits within the lumen of vessel 320 before delivering the drug. As shown in FIG. 3, the device 310 has a catheter portion 330 connected to an expandable diffusion member 340. The catheter portion 330 contains a diffusion member delivery lumen 350 and a drug delivery lumen 360. In the figure, the drug delivery lumen 360 is shown coaxial with the diffusion member delivery lumen 350. But this need not be the case for any embodiments described in this document. For each of the embodiments in this document described as having a diffusion member delivery lumen 350 coaxial with the drug delivery lumen 360, a corresponding embodiment exists in which these lumens are not coaxial.

In operation, the device 310 is placed into a desired vessel 320 upstream of the desired treatment region or organ. The expandable diffusion member 340 is deployed creating a region of increased turbulence in the blood flow near the expandable diffusion member 340. Upstream of the expandable diffusion member 340 within the region of increased blood turbulence or upstream of that region, the can be released from drug delivery lumen 360.

When the drug reaches the turbulent region, it mixes more thoroughly with the blood than it would have if the expandable diffusion member 340 were not present. Past the turbulent region, the blood and drug mixture returns to laminar flow 370. After drug delivery, the expandable diffusion member 340 is retrieved.

Figure 4:
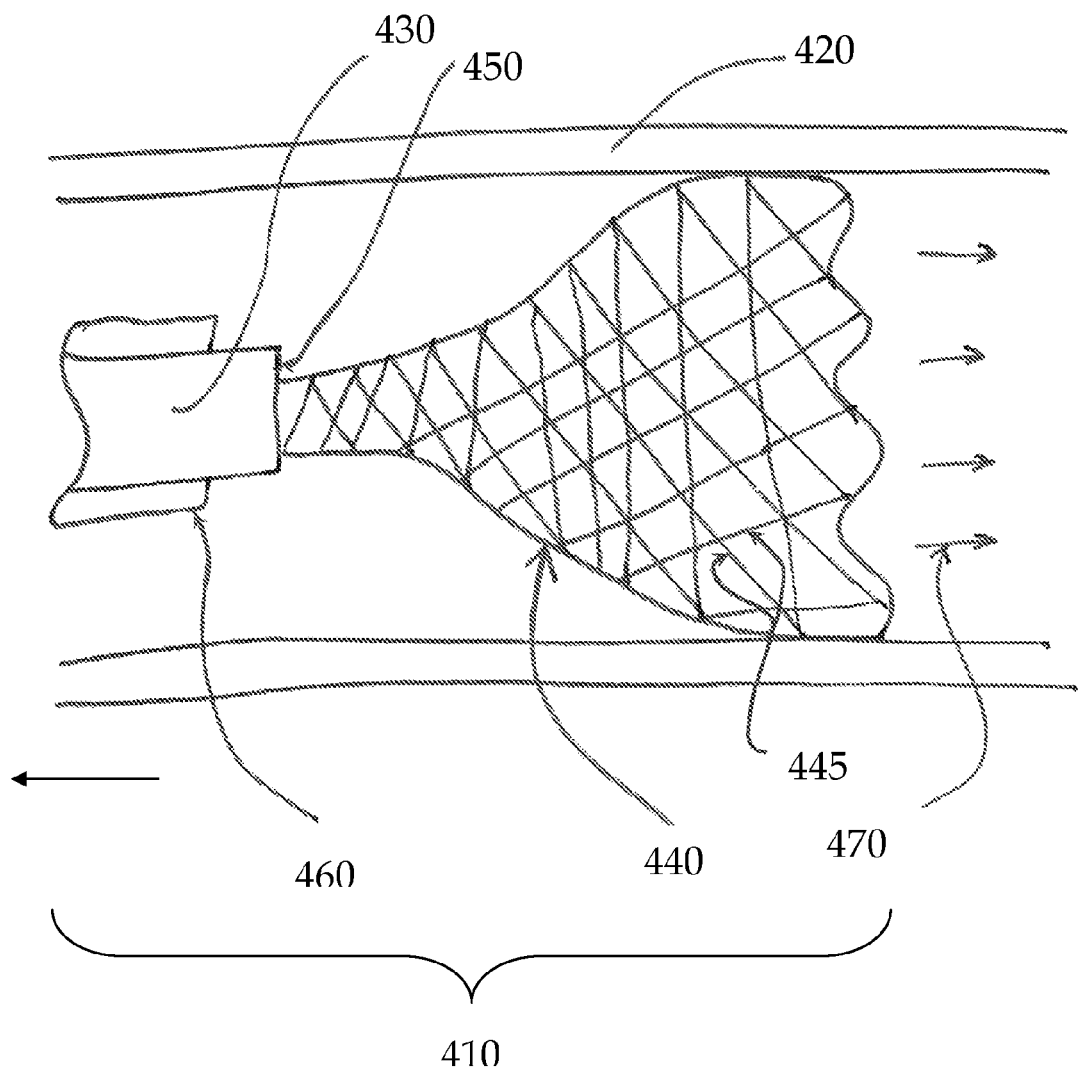
FIG. 4 is a schematic view of a catheter and an embodiment of an expandable diffusion member.

Referring to FIG. 4, the device 410 is situated within the lumen of the vessel 420 before delivering the drug. As shown in FIG. 4, the device 410 has a catheter portion 430 connected to an expandable diffusion member 440. In this embodiment and others like it, the expandable diffusion member 440 is made up of filaments 445 that have been braided or woven to give expandable member 440 a net-like structure.

Stainless steel, silver, platinum, tantalum, palladium, cobalt-chromium alloys such as L605, MP35N, or MP20N, niobium, iridium, any equivalents thereof, alloys thereof, and combinations thereof, nylon, urethane, polyurethane, polyvinylchloride, polyester, PEEK, PTFE, PVDF, Kyner, polyimide, or polyethylene of various suitable densities, nickel titanium, polyamides, silicone modified polyurethanes, fluoropolymers, polyolefins, polyimides, polyimines, (methyl) acrylic polymers, polyesters, polyglycolide, polyglycolide (PGA), poly(L-lactide) (PLLA), poly(D,L-lactide) (PDLLA), poly(L-lactide-co-glycolide) (PLGA), poly(D,L-lactide-co-glycolide) (PDLGA), poly(e-caprolactone) (PCL), polydioxanone, poly(ethylene glycol) (PEG), poly (vinyl alcohol), and co-polymers thereof.

The catheter portion 430 also contains a diffusion member delivery lumen 450 in the drug delivery lumen 460 (shown coaxial to diffusion member delivery lumen 450).

In operation, device 410 is placed into desired vessel 420 upstream of the desired treatment region. The expandable diffusion member 440 is deployed by retracting a sheath (not shown). The expandable diffusion member 440 then self-expands or is expanded to create a net-like structure, essentially as shown in FIG. 4.

In some embodiments, this net-like structure creates a series of objects in the path of the flowing blood, which creates turbulence in the blood flow within a region encompassing the vicinity of the expandable diffusion member 440.

Upstream of the expandable diffusion member 440, either within the region of increased blood turbulence or upstream of it, the drug solution can be released from the drug delivery lumen 460.

When the drug reaches the turbulent region, the net-like structure causes the drug solution and surrounding blood to travel paths around the filaments 445 of the net-like expandable member 440. The change in direction is believed to cause increased mixing between the blood and the drug solution, though the inventors do not wish to be bound by this theory. In any case, the blood mixes with the drug solution and returns to substantially laminar flow 470 downstream of the expandable diffusion member 440. After drug delivery, the expandable diffusion member 440 is covered or retracted to return it to an unexpanded size and is removed from vessel 420.

Figure 5:
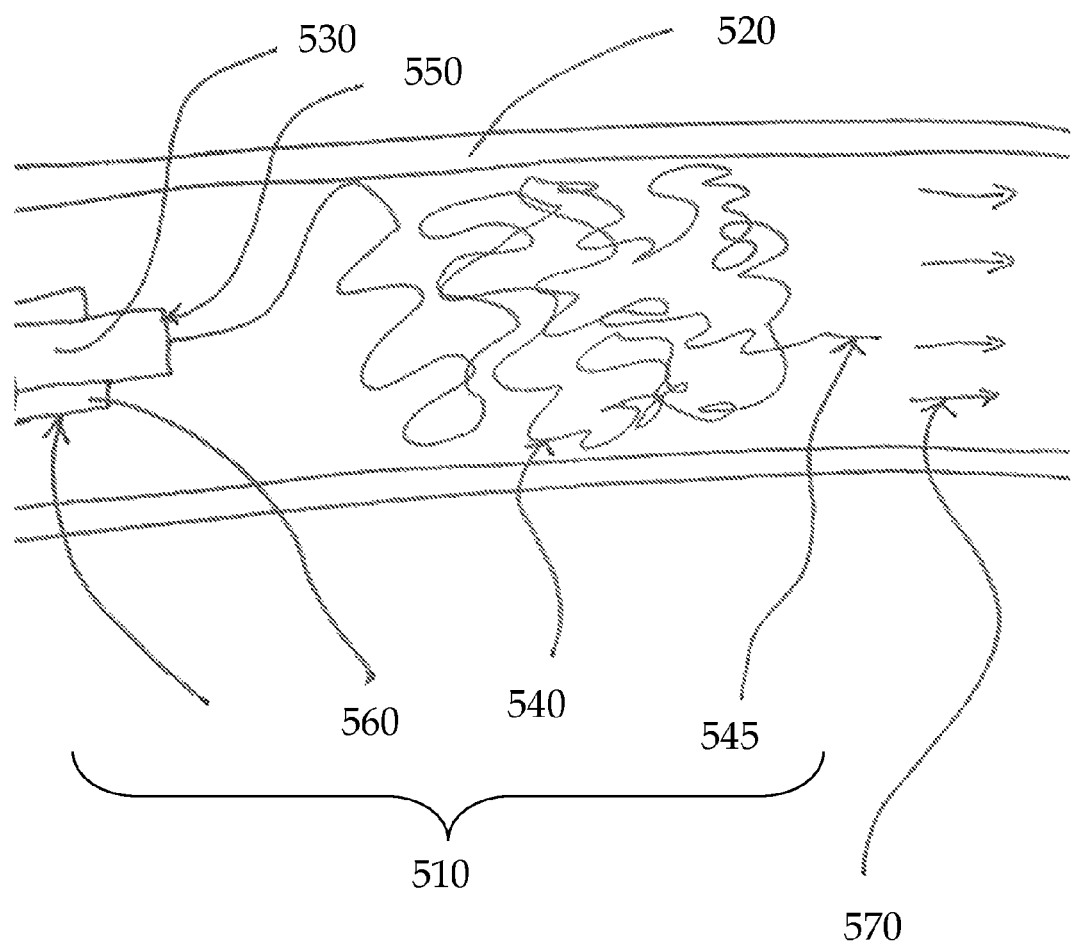
FIG. 5 is a schematic view of a catheter and an embodiment of an expandable diffusion member.

Referring to FIG. 5, the device 510 is situated within the lumen of vessel 520 upstream of the desired treatment region or organ before delivering the drug. As shown in FIG. 5, the device 510 has a catheter portion 530 connected to an expandable diffusion member 540. In this embodiment and others like it, the expandable diffusion member 540 is composed of a shape memory material (such as nitinol) that has been formed into an elongated ball of material containing an atraumatic tip 545.

As one example, the wire may be heat set by wrapping it around a fixture such that it has the desired shape, and then the fixture may be inserted within a heated salt bath or other environment at 400-500 degrees Celsius for approximately 1-15 minutes. The fixture may be removed from the heated environment to quench the wire and then the shaped wire may be removed from the fixture. The wire may be straightened simply by placing it within the lumen of a straightened catheter. When the wire is advanced from the catheter, it will resume the set shape.

Alternatively, the wire may be straightened by applying tension to the entangled portion of the wire. After straightening the wire, it may be shape set by subjecting the wire to cooling below its transition temperature, which varies based on the percentage composition of material constituents. When the wire is advanced into the blood stream, its temperature will rise above the transition point and it will resume the set shape.

Other shape memory materials include: copper-zinc-aluminum and copper-aluminum-nickel (note that these may not be ideal for medical use), biodegradable polymers, such as oligo(ε-caprolactone)diol, oligo(ρ-dioxanone)diol, and non-biodegradable polymers such as, polynorborene, polyisoprene, styrene butadiene, polyurethane-based materials, vinyl acetate-polyester-based compounds, and others yet to be determined.

The catheter portion 530 also contains a diffusion member delivery lumen 550 and a drug delivery lumen 560 (shown coaxial to diffusion member delivery lumen 550).

In operation, the device 510 is placed into a desired vessel 520 upstream of the desired treatment region or organ. The expandable diffusion member 540 is deployed by slowly pushing the wire or filament of shape memory material out of the distal end of the device 510 through the diffusion member delivery lumen 550. As the shape memory material enters the blood environment, the blood warms it above its phase transition temperature, which causes it to return to the shape that it had before being straightened—to return to an elongated ball of wire or filament.

In some embodiments, the elongated ball is similar to a ball of steel wool. Thus, it creates a multiplicity of fluid paths from the semi-random wire or filament structure now located in the lumen of vessel 520. The act of forcing the blood to take many paths that separate, reform, and cross each other as it moves through the elongated ball of shape memory material creates a region of turbulent blood flow in the vicinity of the ball of shape memory material (composing the expandable diffusion member 540).

Upstream of the expandable diffusion member 540 and, in some embodiments, upstream of the turbulent region, the drug emerges from the drug delivery lumen 560.

When the drug reaches the turbulent region, the turbulence causes it to mix with the blood better than if the expandable diffusion member 540 were not present. At some point downstream of the turbulent region, the blood and drug mixture returns to substantially laminar flow 570.

Once drug delivery is completed, the expandable diffusion member 540 is removed from the lumen of the vessel 520 by retracting the wire or filament back into the diffusion delivery lumen 550.

Figure 6:
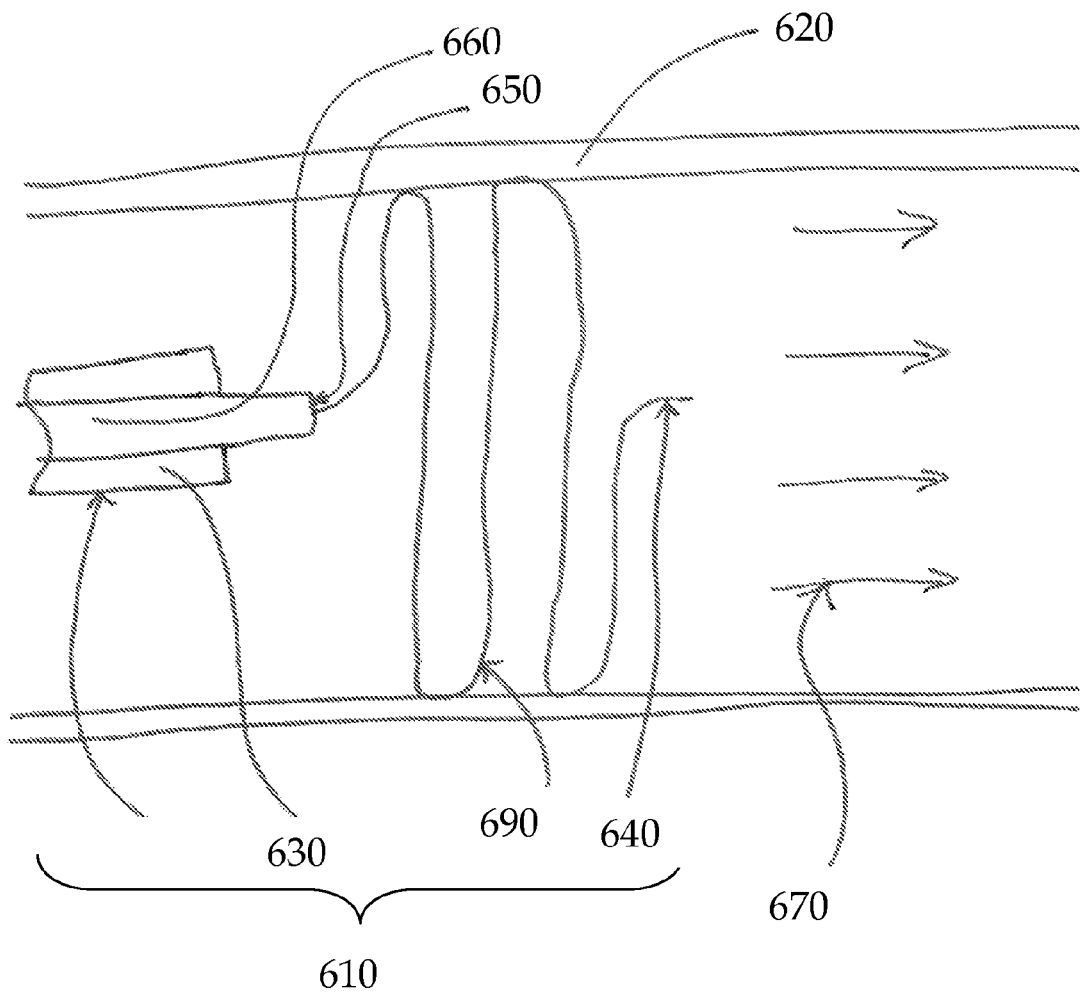
FIG. 6 is a schematic side view of the catheter and an embodiment of an expandable diffusion member.

Referring to FIG. 6, the device 610 is situated in the lumen of vessel 620 upstream of the desired treatment region or organ before drug delivery. As shown in FIG. 6, the device 610 has catheter portion 630 connected to expandable diffusion member 640. In this embodiment, and others like it, the expandable diffusion member 640 is constructed from a filament or wire of shape memory material, such as nitinol. As seen in FIG. 6, the expandable diffusion member 640 is shaped into one or more planar, serpentine curves 690 that substantially occupy the space between the walls of the lumen of vessel 620. In some embodiments, the plane that contains a serpentine curve 690 is substantially perpendicular to the direction of blood flow. For those embodiments with more than one set of planes of serpentine curves 690, curves of subsequent planes can be aligned in the same direction as the serpentine curves 690 in the first plane or they can be aligned in different directions.

Figure 7:
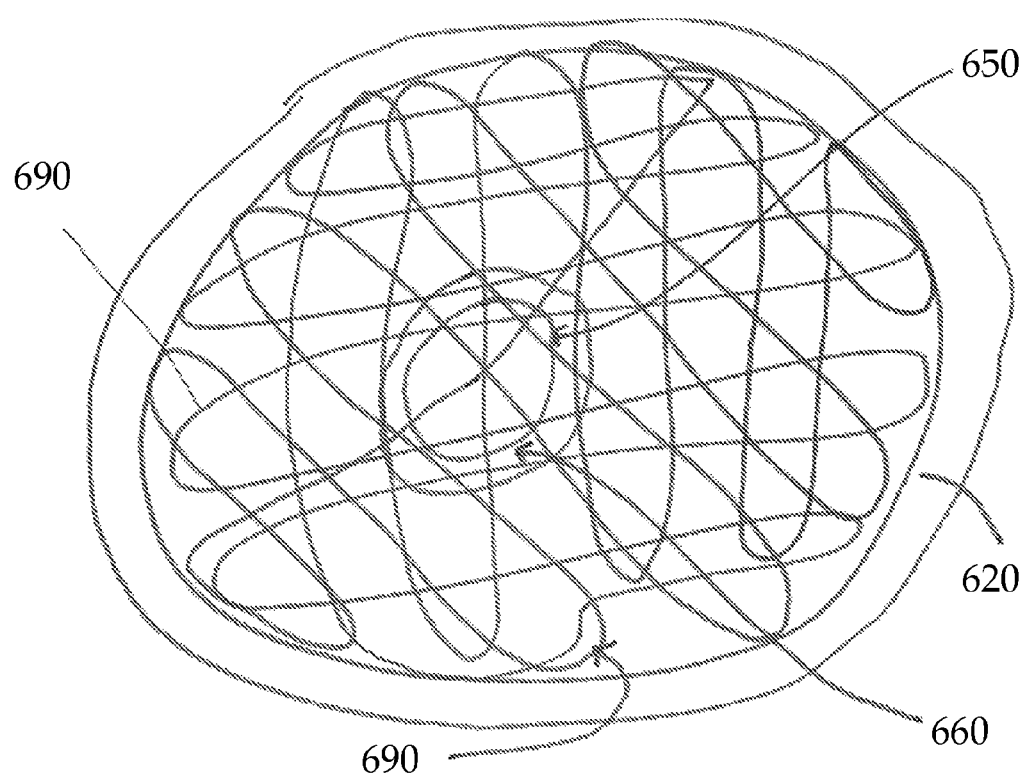
FIG. 7 is a schematic view of the distal end, in cross-section, of the catheter and expandable diffusion member of FIG. 6.

As seen in FIG. 7 device 610 has diffusion member delivery lumen 650 seen end on. The figure also shows that the device 610 has a drug delivery lumen 660, seen end on. Both the diffusion member delivery lumen 650 and the drug delivery lumen 660 are situated upstream of expandable diffusion member 640.

In operation, the device 610 is placed into desired vessel 620 upstream of the desired treatment region or organ. The expandable diffusion member 640 is deployed by slowly pushing the wire or filament of shape memory material out of the distal end of the device 610 through the diffusion member delivery lumen 650. As the shape memory material enters the blood environment, the blood warms it above its phase transition temperature causing the material to return to the shape that it had before being straightened—to return to a substantially regular plane or substantially regular planes of serpentine curves 690.

In some embodiments, the serpentine curves are similar to a screen. Thus, they create a multiplicity of fluid paths from the screen structure now located in the lumen of vessel 620. The act of forcing the blood to take many paths that separate, reform, and cross each other as it flows through the screen of shape memory material creates a region of turbulent blood flow in the vicinity of the screen of shape memory material (composing the expandable diffusion member 640).

Upstream of the expandable diffusion member 640 and, in some embodiments, upstream of the turbulent region, drug emerges from the drug delivery lumen 660.

When the drug reaches the turbulent region, the turbulence causes it to mix with the blood better than if the expandable diffusion member 640 were absent. At some point downstream of the turbulent region, the blood and drug mixture returns to substantially laminar flow 670.

Once drug delivery is completed, the expandable diffusion member 640 is removed from the lumen of the vessel 620 by retracting the wire or filament back into the diffusion delivery lumen 650.

Figure 8:
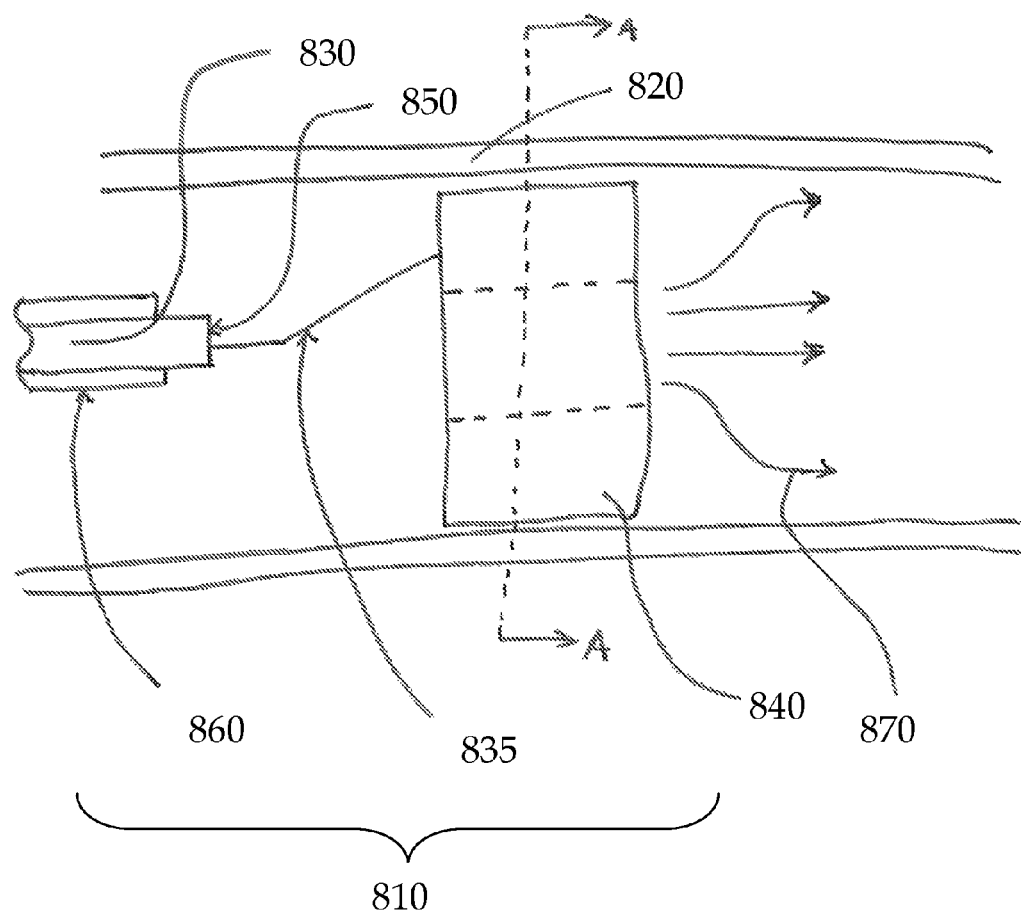
FIG. 8 is a schematic view of the catheter and an embodiment of an expandable diffusion member.

Referring to FIG. 8, the device 810 is situated within the lumen of vessel 820 before drug delivery. As shown in FIG. 8, the device 810 has a catheter portion 830 connected, through a control arm 835, to an expandable diffusion member 840. This expandable diffusion member 840 has a toric or donut shape. This donut structure can be rigid or semi-rigid, metallic, polymeric, foam, or of any other suitable construction or structure as one of ordinary skill in the art would recognize from the object's function.

The catheter portion 830 contains a diffusion member delivery lumen 850 and a drug delivery lumen 860. In the figure, the drug delivery lumen 860 is shown coaxial with the diffusion member delivery lumen 850.

In operation, the device 810 is placed into desired vessel 820 upstream of the desired treatment region or organ. The expandable diffusion member 840 is deployed creating a region of increased turbulence in the blood flow in the vicinity of the expandable diffusion member 840. Upstream of the expandable diffusion member 840 within the region of increased blood turbulence or upstream of that region, drug or drug solution can be released from drug delivery lumen 860.

When the drug reaches the turbulent region, it mixes more thoroughly with the blood than it would have if the expandable diffusion member 840 were not present. After the turbulent region, the blood and drug mixture returns to laminar flow 870.

After drug delivery, the expandable diffusion member 840 is retrieved.

Figure 9:
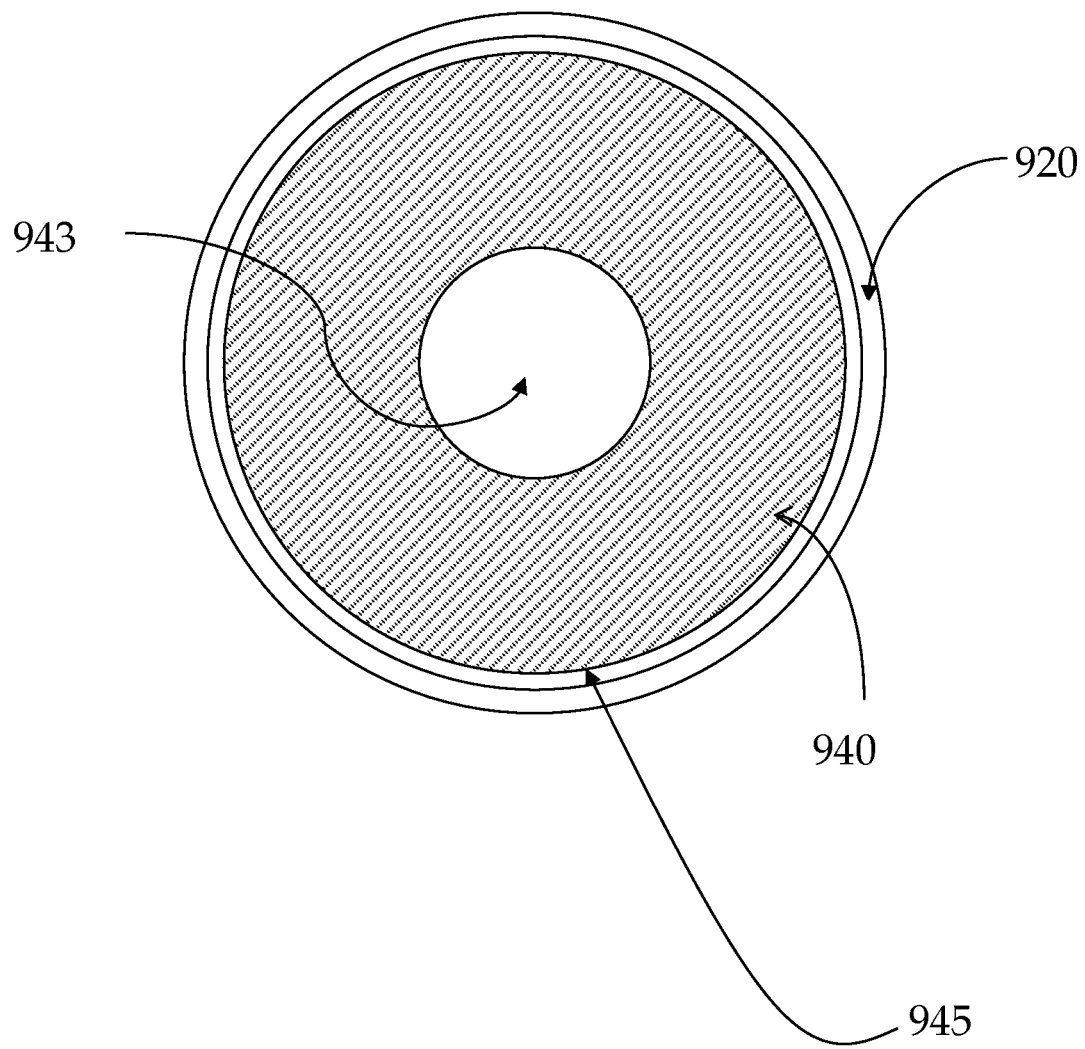
FIG. 9 is a cross-section taken along the A-A plane of FIG. 8 showing an embodiment of an expandable diffusion member.

The expandable diffusion member 840 has a toric or donut shape with a passage 943. In some embodiments, the outer wall 945 of the toric expandable diffusion member 940 presses against the walls of vessel 920. This can be seen in FIG. 9. In other embodiments the outer wall 945 of the toric expandable diffusion member 940 ends substantially short of the walls of vessel 920.

This fitment between the outer wall 945 and the walls of vessel 920 either prevents or allows blood to pass between the outer wall 945 and the walls of vessel 920 depending on which embodiment of the two described is under consideration. For embodiments with close fitment between the outer wall 945 of the toric expandable diffusion member 940, all of the blood flow to the vessel is routed through the center of the expandable diffusion member 940. For those embodiments with loose fitment between the outer wall 945 of the expandable diffusion member 940, some blood flows between the outer wall 945 and the walls of vessel 920 and some blood flows through the passageway 943 in the toric expandable diffusion member 940. For both embodiments, the toric expandable diffusion member 940 causes a velocity change in the blood flow creating a turbulent region of blood near the expandable diffusion member 940.

Each of the embodiments described above comprising an expandable diffusion member can be combined with an upstream occlusion balloon. The occlusion balloon is used to temporarily stop blood flow through a vessel. Occlusion occurs when the balloon is inflated and seals against the vessel wall.

Treatment Agents

As used in this document, treatment agents are intended to include, but are not limited to, drugs, biologically active agents, chemically active agents, therapeutic agents, and the like, and pharmaceutical compositions thereof, which can be used to deliver a treatment agent to a treatment site within a kidney as described in this document. Treatments agents may contain a mixture of active agents.

In one embodiment, the treatment agent may include a property to inhibit a biological process contributing to nephropathy. Such biological processes may include, but are not limited to, changes in glomerular basement membrane, changes in mesangial matrix deposition and podocyte attachment or apoptosis.

In one embodiment, the treatment agent may include a drug. The drug may have a property to inhibit undesirable effects of the renin-angiotensin system in the kidneys. The renin-angiotensin system responds to a decrease in the perfusion of the juxtaglomerular apparatus found in afferent arterioles of the glomerulus of the kidney by constricting glomerular arterioles. Such constriction causes blood to build up in the glomerulus and increase glomerular pressure. Representative drugs that may act to inhibit this process include, but are not limited to, angiotensin converting enzyme (ACE) inhibitors, angiotensin receptor blockers (ARBs) and renin inhibitors.

In still further embodiments, the treatment agent may include a drug to inhibit protein kinase C. Representative drugs may include, but are not limited to, ruboxistaurin (LY333531), enzastaurin (LY317615), bisindolylmaleimide IX, chelerythrine, edelfosine, edelfosina, ET180CH3, H-7, HA-100, H89, HA-1004, Ro 31-8220, rottlerin, staurosporine and quercetin.

The transforming-growth-factor-beta system contributes to the progression of renal damage due to stimulation of extracellular matrix deposition. Thus, in some embodiments, the treatment agent may include an agent having a property to inhibit transforming growth factor beta, its receptor and SMAD and other signaling molecules downstream of the receptor. Representative inhibitors may include, but are not limited to antisense molecules, ribozymes, siRNA, antibodies, receptor kinase inhibitors and other small molecule inhibitors such as halofuginone, sirolimus, everolimus, biolimus ABT578 and nuclear receptor agonists such as estradiol, retinoids, and peroxisome proliferator-activated receptors (PPAR) agonists.

It is further recognized that connective tissue growth factor (CTGF) is present in glomeruli in patients with diabetic nephropathy. CTGF is a member of the centrosomin (CCN) family of proteins, which regulate biological processes including stimulation of cell proliferation, migration, and adhesion. Probably, expression of CTGF in diabetic kidneys contributes to the development of glomerulosclerosis by affecting matrix synthesis and its turnover. In this aspect, the treatment agent may include an agent having a property to inhibit connective tissue growth factor. Representative agents having a property to inhibit connective tissue growth factor may include, but are not limited to antibodies, interleukin-1 (IL-1) alpha and beta, Rho A GTPase inhibitors, and p38 MAP kinase inhibitors.

In some embodiments, the treatment agent may be modified to enhance its uptake into the desired tissue. In this aspect, the treatment agent may be delivered to the desired tissue in a formulation that may include vasoactive agents as enhancers of vascular permeability called excipients, such as thrombin, bradykinin and histamine. These excipients have properties that increase endothelial porosity and thereby enhance uptake of the treatment agent into the tissue.

The treatment agent may be delivered in a form including, but not limited to, a solution. For example, in some embodiments, a desired amount of treatment agent is mixed with saline or an iodine-free contrast media to form the solution.

In some embodiments, the treatment agent may be delivered to the desired tissue in a carrier. In one aspect, the carrier may be a sustained-release carrier that allows for controlled release of the treatment agent over time at the desired treatment site. "Carrier" includes a matrix that contains one or more treatment agents. A suitable carrier may take the form of a nanoparticle (e.g., nanosphere), microparticle (e.g., microsphere) or liposome as the situation may dictate. The carrier with encapsulated treatment agent may be incorporated into a solution including an oily material for delivery to the desired tissue.

The carrier may be a bioerodable carrier (sometimes used interchangeably with "sustained-release carriers") infused with a treatment agent. Suitable materials for sustained-release carriers include, but are not limited to, encapsulation polymers such as poly (L-lactide), poly (D,L-lactide), poly (glycolide), poly (lactide-co-glycolide), polycaprolactone, polyanhydride, polydioxanone, polyorthoester, polyamino acids, or poly (trimethylene carbonate), and combinations of these materials.

Treatment agents, including treatment agents combined with a carrier (e.g., a sustained release carrier), having a size greater than about 10 microns can become trapped in the glomerular capillaries when introduced into the renal artery. In this aspect, the treatment agent may be released over time at a point within the glomerular capillaries. In other embodiments, the carrier size may be between about 1 micron to 100 microns, still further between about 8 microns to about 15 microns and in some embodiments between about 1 micron to 2 microns. In other embodiments, the carrier size may be between about 10 microns and 14 microns. In still further embodiments where the treatment agent is delivered at a point outside of a vessel lumen, such as the kidney cortex, the treatment agent or a carrier encapsulating the treatment agent may be any size capable of being delivered through a lumen of the delivery device, such as for example, a size as small as one nanometer to as large as about 100 microns.

Various methods may be employed to formulate and infuse the carrier with one or more treatment agents. The embodiments of the composition of infused carrier may be prepared by conventional methods where all components are combined then blended. In some embodiments, carriers may be prepared using a predetermined amount of a polymer or a prepolymer that is added to a predetermined amount of a solvent or a combination of solvents. The solvent is mutually compatible with the polymer and is capable of dissolving the polymer into solution at the desired concentration. Examples of solvents may include, but are not limited to, dimethylsulfoxide (DMSO), Dimethyl Acetamide (DMAC), chloroform, acetone, water (buffered saline), xylene, acetone, methanol, ethanol, 1-propanol, tetrahydrofuran, 1-butanone, dimethylformamide, dimethylacetamide, cyclohexanone, ethyl acetate, methylethylketone, propylene glycol monomethylether, isopropanol, N-methyl pyrrolidinone, toluene and mixtures of these materials.

By way of example, and not limitation, the polymer may comprise from about 0.1% to about 35%, more narrowly about 2% to about 20% by weight of the total weight of the total solution, and the solvent may comprise from about 65% to about 99.9%, more narrowly about 80% to about 98% by weight, of the total weight of the total solution. Specific weight ratios depend on factors such as the material from which the delivery device is made and the geometrical structure of the device.

Sufficient amounts of treatment agent are dispersed or dissolved in the carrier. The amount of treatment agent introduced into the carrier may be any amount sufficient to inhibit a biological process, such as a biological process contributing to nephropathy, when released within the renal system. The treatment agent may be dissolved or suspended. If the treatment agent is not completely soluble in the composition, operations including mixing, stirring, or agitation may be employed to effect homogeneity. The treatment agent may be added so that the dispersion is in fine particles. The mixing of the treatment agent may be conducted in an anhydrous atmosphere, at ambient pressure and at room temperature.

In some embodiments using microparticles or nanoparticles, the microparticles or nanoparticles may be sustained release carriers prepared by a water/oil/water (WOW) double emulsion method. The WO phase, an aqueous phase containing treatment agent, is dispersed into the oil phase containing polymer dissolved in organic solvent (e.g., dichloromethane) using a high-speed homogenizer. Examples of sustained-release polymers that may be used include, but are not limited to, poly(D,L-lactide-co-glycolide) (PLGA), poly(D,L-lactide) (PLA) or PLA-PEEP co-polymers, poly-ester-amide co-polymers (PEA) and polyphophazines. The primary water-in-oil (WO) emulsion is then dispersed to an aqueous solution containing a polymeric surfactant, e.g., poly(vinyl alcohol) (PVA), and further homogenized to produce a WOW emulsion. After stirring for several hours, the microparticles or nanoparticles are collected by filtration.

In some embodiments, the sustained-release carrier is a liposome. "Liposomes" are approximately spherical artificial vesicles and can be produced from natural phospholipids and cholesterol. In one method, phospholipids are mixed with cholesterol in chloroform. Suitable phospholipids include, but are not limited to, dimyristoyl phosphatidyl choline or dipalmitoyl phosphatidyl ethanolamine. In some embodiments, a hydrophobic treatment agent may be added with an optional co-solvent. After mixing, the solvent (and optional co-solvent) may be evaporated with heat or ambient temperature in a round bottom flask. Resultant lipids may be deposited on the glass surface. In some embodiments, a hydrophilic treatment agent and water may be added to the flask and sonicated to form liposomes. The resultant solution may be pressure filtered through ceramic pore size controlled filters to reduce liposome particle size. In still further embodiments, the carrier is a micro-bubble formed by any technique deemed desirable.

In some embodiments, a surface of the carrier may be modified to enhance affinity of the encapsulated treatment agent to tissue lining the walls of the glomerular capillaries. In this aspect, the surface may be coated with binding agents. The binding agent may include a protein or small molecule that will facilitate retention of the carrier and encapsulated treatment agent at the treatment site to induce or modulate a therapeutic response through interaction with a specific binding site (e.g., a receptor within a cell or on a cell surface). Representative binding agents and their associated receptors include, but are not limited to, CD1 lb/CD1 8 (MAC-1) or aL/beta2 integrin (LFA-1) and intracellular adhesion molecule-1 (ICAM-1) receptor, integrin avb3 which binds to RGD-containing peptide and E-selectin which binds to Sialyl-Lewis glycoprotein.

A surface charge of the carrier may further be modified (e.g. positively, negatively or neutral) to accommodate and enhance binding characteristics to the glomerular tissue. The endothelial cells and basement membrane along the normal glomerular capillary walls are typically electronegatively charged. As diseases such as glomerulosclerosis and diabetic nephropathy progress, however, these cells slowly lose the electronegative charge. It is believed that modifying the carriers to have an electropositive charge will enhance binding of the carrier and encapsulated agent to the cells or membrane.

In this aspect, a carrier encapsulating the treatment agent may be modified by any standard method suitable for providing the carrier surface with an electropositive charge. In one embodiment, positively charged carriers may be synthesized by coating carriers with Chitosan. Alternatively, positively charged carriers may be made, for example, entirely of Chitosan in a water-in-oil emulsion process and crosslinked with glutaraldehye or genipin. In this aspect, the treatment agent may be swell-loaded in the crosslinked spheres. Still further, if the treatment agent is soluble at pH 5, the treatment agent may be incorporated into the initial Chitosan solution, if it does not subsequently react with the aldehyde crosslinker. Another approach for forming cationic carriers may include using a polylysine graft of PLGA.

In still further embodiments, a surface of the carrier may be coated with active agents or other species to enhance the range of functionalities of the product. For example, the surface may be coated with a monoclonal antibody that selectively binds to proteins expressed within the glomerulus (glomerular endothelium, basement membrane, podocytes) and tubules (tubular epithelium and basement membrane). A representative example is the monoclonal antibody anti CD90/Thy 1 that binds to OX-7 a glomerular basement membrane protein. Other useful proteins include nephrin and podocin.

The following aspects are representative. They disclose various features or combination of features as examples only and are not intended to limit the more general description of the invention as described above and in the claims.

Aspect (1)—A device comprising a catheter including a main body, an expandable diffusion member comprising a body, and a drug delivery lumen.

Aspect (2)—The device of aspect 1 wherein the expandable diffusion member comprising a body comprises a preformed shape memory material.

Aspect (3)—The device of aspect 2 wherein the preformed shape memory material comprises nitinol.

Aspect (4)—The device of aspect 1 wherein the expandable diffusion member comprising a body comprises a net-like, braided structure.

Aspect (5)—The device of aspect 4 wherein the net-like, braided structure comprises one, two, or more wires or filaments.

Aspect (6)—The device of aspect 1 wherein the expandable diffusion member comprising a body comprises a donut structure.

Aspect (7)—The device of aspect 6 wherein the donut structure comprises a body with a cylinder with a length and a passage coaxial to the cylindrical axis.

Aspect (8)—The device of aspect 7 wherein the length ranges from one to ten times the largest diameter of the body.

Aspect (9)—The device of aspect 8 wherein the cylinder has a diameter of 50-105% of the vessel.

Aspect (10)—The device of aspect 9 wherein the passage has a diameter that ranges from 15-80% of the diameter of the cylinder.

Aspect (11)—The device of aspect 10 further comprising a connecting member that joins the main body to the expandable diffusion member comprising a body.

Aspect (12)—The device of aspect 7 further comprising a connecting member that joins the main body to the expandable diffusion member comprising a body.

Aspect (13)—The device of aspect 12 wherein the length ranges from one to ten times the largest diameter of the body.

Aspect (14)—The device of aspect 13 wherein the cylinder has a diameter of 50-105% of the vessel.

Aspect (15)—The device of aspect 15 wherein the passage has a diameter that ranges from 15-80% of the diameter of the cylinder.

Aspect (16)—The device of aspect 1 wherein the expandable diffusion member has a body with a length wherein the length ranges from one to ten times the largest diameter of the body.

Aspect (17)—The device of aspect 7 wherein the cylinder has a diameter of 50-105% of the vessel.

Aspect (18)—The device of aspect 7 wherein the passage has a diameter that ranges from 15-80% of the diameter of the cylinder.

Aspect (19)—The device of aspect 1 wherein the expandable diffusion member comprising a body further comprises a ball of wire or filament.

Aspect (20)—The device of aspect 19 wherein the ball of wire or filament comprises a set of coplanar serpentine curves.

Aspect (21)—The device of aspect 20 wherein the ball of wire or filament comprises two or more sets of one or more coplanar, serpentine curves each set situated in different planes.

Aspect (22)—The device of aspect 21 further comprising two or more sets of one or more coplanar, serpentine curves each set situated in different planes wherein one or more sets of planes are substantially parallel to each other.

Aspect (23)—The device of aspect 1 wherein the expandable diffusion member comprising a body further comprises an occlusion balloon.

Aspect (24)—The device of aspect 1 wherein the devise further comprises an occlusive device proximal to the drug delivery lumen.

Aspect (25)—The device of aspect 2 wherein the devise further comprises an occlusive device proximal to the drug delivery lumen.

Aspect (26)—The device of aspect 3 wherein the devise further comprises an occlusive device proximal to the drug delivery lumen.

Aspect (27)—The device of aspect 4 wherein the devise further comprises an occlusive device proximal to the drug delivery lumen.

Aspect (28)—The device of aspect 5 wherein the devise further comprises an occlusive device proximal to the drug delivery lumen.

Aspect (29)—The device of aspect 6 wherein the devise further comprises an occlusive device proximal to the drug delivery lumen.

Aspect (30)—The device of aspect 7 wherein the devise further comprises an occlusive device proximal to the drug delivery lumen.

Aspect (31)—The device of aspect 8 wherein the devise further comprises an occlusive device proximal to the drug delivery lumen.

Aspect (32)—The device of aspect 9 wherein the devise further comprises an occlusive device proximal to the drug delivery lumen.

Aspect (33)—The device of aspect 10 wherein the devise further comprises an occlusive device proximal to the drug delivery lumen.

Aspect (34)—The device of aspect 11 wherein the devise further comprises an occlusive device proximal to the drug delivery lumen.

Aspect (35)—The device of aspect 12 wherein the devise further comprises an occlusive device proximal to the drug delivery lumen.

Aspect (36)—The device of aspect 13 wherein the devise further comprises an occlusive device proximal to the drug delivery lumen.

Aspect (37)—The device of aspect 14 wherein the devise further comprises an occlusive device proximal to the drug delivery lumen.

Aspect (38)—The device of aspect 15 wherein the devise further comprises an occlusive device proximal to the drug delivery lumen.

Aspect (39)—The device of aspect 16 wherein the devise further comprises an occlusive device proximal to the drug delivery lumen.

Aspect (40)—The device of aspect 17 wherein the devise further comprises an occlusive device proximal to the drug delivery lumen.

Aspect (41)—The device of aspect 18 wherein the devise further comprises an occlusive device proximal to the drug delivery lumen.

Aspect (42)—The device of aspect 19 wherein the devise further comprises an occlusive device proximal to the drug delivery lumen.

Aspect (43)—The device of aspect 20 wherein the devise further comprises an occlusive device proximal to the drug delivery lumen.

Aspect (44)—The device of aspect 21 wherein the devise further comprises an occlusive device proximal to the drug delivery lumen.

Aspect (45)—The device of aspect 22 wherein the devise further comprises an occlusive device proximal to the drug delivery lumen.

Aspect (46)—The device of aspect 23 wherein the devise further comprises an occlusive device proximal to the drug delivery lumen.

Aspect (47)—A method comprising delivering a portion of a device to a blood vessel wherein the device comprises a catheter including a main body, an expandable diffusion member comprising a body, and a drug delivery lumen.

Aspect (48)—The method of aspect 47 wherein the expandable diffusion member comprising a body comprises a pre-formed shape memory material.

Aspect (49)—The method of aspect 48 wherein the pre-formed shape memory material comprises nitinol.

Aspect (50)—The method of aspect 47 wherein the expandable diffusion member comprising a body comprises a net-like, braided structure.

Aspect (51)—The method of aspect 50 wherein the net-like, braided structure comprises one, two, or more wires or filaments.

Aspect (52)—The method of aspect 47 wherein the expandable diffusion member comprising a body comprises a donut structure.

Aspect (53)—The method of aspect 52 wherein the donut structure comprises a body with a cylinder with a length and a passage coaxial to the cylindrical axis.

Aspect (54)—The method of aspect 53 wherein the length ranges from one to ten times the largest diameter of the body.

Aspect (55)—The method of aspect 54 wherein the cylinder has a diameter of 50-105% of the vessel.

Aspect (56)—The method of aspect 55 wherein the passage has a diameter that ranges from 15-80% of the diameter of the cylinder.

Aspect (57)—The method of aspect 56 further comprising a connecting member that joins the main body to the expandable diffusion member comprising a body.

Aspect (58)—The method of aspect 53 further comprising a connecting member that joins the main body to the expandable diffusion member comprising a body.

Aspect (59)—The method of aspect 58 wherein the length ranges from one to ten times the largest diameter of the body.

Aspect (60)—The method of aspect 59 wherein the cylinder has a diameter of 50-105% of the vessel.

Aspect (61)—The method of aspect 60 wherein the passage has a diameter that ranges from 15-80% of the diameter of the cylinder.

Aspect (62)—The method of aspect 47 wherein the expandable diffusion member has a body with a length wherein the length ranges from one to ten times the largest diameter of the body.

Aspect (63)—The method of aspect 53 wherein the cylinder has a diameter of 50-105% of the vessel.

Aspect (64)—The method of aspect 53 wherein the passage has a diameter that ranges from 15-80% of the diameter of the cylinder.

Aspect (65)—The method of aspect 47 wherein the expandable diffusion member comprising a body further comprises a ball of wire or filament.

Aspect (66)—The method of aspect 65 wherein the ball of wire or filament comprises a set of coplanar serpentine curves.

Aspect (67)—The method of aspect 66 wherein the ball of wire or filament comprises two or more sets of one or more coplanar, serpentine curves each set situated in different planes.

Aspect (68)—The method of aspect 67 further comprising two or more sets of one or more coplanar, serpentine curves each set situated in different planes wherein one or more sets of planes are substantially parallel to each other.

Aspect (69)—The method of aspect 47 wherein the expandable diffusion member comprising a body further comprises an occlusion balloon.

Aspect (70)—The method of aspect 47 wherein the devise further comprises an occlusive device proximal to the drug delivery lumen.

Aspect (71)—The method of aspect 48 wherein the devise further comprises an occlusive device proximal to the drug delivery lumen.

Aspect (72)—The method of aspect 49 wherein the devise further comprises an occlusive device proximal to the drug delivery lumen.

Aspect (73)—The method of aspect 50 wherein the devise further comprises an occlusive device proximal to the drug delivery lumen.

Aspect (74)—The method of aspect 51 wherein the devise further comprises an occlusive device proximal to the drug delivery lumen.

Aspect (75)—The method of aspect 52 wherein the devise further comprises an occlusive device proximal to the drug delivery lumen.

Aspect (76)—The method of aspect 53 wherein the devise further comprises an occlusive device proximal to the drug delivery lumen.

Aspect (77)—The method of aspect 54 wherein the devise further comprises an occlusive device proximal to the drug delivery lumen.

Aspect (78)—The method of aspect 55 wherein the devise further comprises an occlusive device proximal to the drug delivery lumen.

Aspect (79)—The method of aspect 56 wherein the devise further comprises an occlusive device proximal to the drug delivery lumen.

Aspect (80)—The method of aspect 57 wherein the devise further comprises an occlusive device proximal to the drug delivery lumen.

Aspect (81)—The method of aspect 58 wherein the devise further comprises an occlusive device proximal to the drug delivery lumen.

Aspect (82)—The method of aspect 59 wherein the devise further comprises an occlusive device proximal to the drug delivery lumen.

Aspect (83)—The method of aspect 60 wherein the devise further comprises an occlusive device proximal to the drug delivery lumen.

Aspect (84)—The method of aspect 61 wherein the devise further comprises an occlusive device proximal to the drug delivery lumen.

Aspect (85)—The method of aspect 62 wherein the devise further comprises an occlusive device proximal to the drug delivery lumen.

Aspect (86)—The method of aspect 63 wherein the devise further comprises an occlusive device proximal to the drug delivery lumen.

Aspect (87)—The method of aspect 64 wherein the devise further comprises an occlusive device proximal to the drug delivery lumen.

Aspect (88)—The method of aspect 65 wherein the devise further comprises an occlusive device proximal to the drug delivery lumen.

Aspect (89)—The method of aspect 66 wherein the devise further comprises an occlusive device proximal to the drug delivery lumen.

Aspect (90)—The method of aspect 67 wherein the devise further comprises an occlusive device proximal to the drug delivery lumen.

Aspect (91)—The method of aspect 68 wherein the devise further comprises an occlusive device proximal to the drug delivery lumen.

Aspect (92)—The method of aspect 69 wherein the devise further comprises an occlusive device proximal to the drug delivery lumen.

Aspect (93)—The method of aspect 47 wherein delivering comprises delivering the device upstream of a bifurcation in the vessel.

Aspect (94)—The method of aspect 48 wherein delivering comprises delivering the device upstream of a bifurcation in the vessel.

Aspect (95)—The method of aspect 49 wherein delivering comprises delivering the device upstream of a bifurcation in the vessel.

Aspect (96)—The method of aspect 50 wherein delivering comprises delivering the device upstream of a bifurcation in the vessel.

Aspect (97)—The method of aspect 51 wherein delivering comprises delivering the device upstream of a bifurcation in the vessel.

Aspect (98)—The method of aspect 52 wherein delivering comprises delivering the device upstream of a bifurcation in the vessel.

Aspect (99)—The method of aspect 53 wherein delivering comprises delivering the device upstream of a bifurcation in the vessel.

Aspect (100)—The method of aspect 54 wherein delivering comprises delivering the device upstream of a bifurcation in the vessel.

Aspect (101)—The method of aspect 55 wherein delivering comprises delivering the device upstream of a bifurcation in the vessel.

Aspect (102)—The method of aspect 56 wherein delivering comprises delivering the device upstream of a bifurcation in the vessel.

Aspect (103)—The method of aspect 57 wherein delivering comprises delivering the device upstream of a bifurcation in the vessel.

Aspect (104)—The method of aspect 58 wherein delivering comprises delivering the device upstream of a bifurcation in the vessel.

Aspect (105)—The method of aspect 59 wherein delivering comprises delivering the device upstream of a bifurcation in the vessel.

Aspect (106)—The method of aspect 60 wherein delivering comprises delivering the device upstream of a bifurcation in the vessel.

Aspect (107)—The method of aspect 61 wherein delivering comprises delivering the device upstream of a bifurcation in the vessel.

Aspect (108)—The method of aspect 62 wherein delivering comprises delivering the device upstream of a bifurcation in the vessel.

Aspect (109)—The method of aspect 63 wherein delivering comprises delivering the device upstream of a bifurcation in the vessel.

Aspect (110)—The method of aspect 64 wherein delivering comprises delivering the device upstream of a bifurcation in the vessel.

Aspect (111)—The method of aspect 65 wherein delivering comprises delivering the device upstream of a bifurcation in the vessel.

Aspect (112)—The method of aspect 66 wherein delivering comprises delivering the device upstream of a bifurcation in the vessel.

Aspect (113)—The method of aspect 67 wherein delivering comprises delivering the device upstream of a bifurcation in the vessel.

Aspect (114)—The method of aspect 68 wherein delivering comprises delivering the device upstream of a bifurcation in the vessel.

Aspect (115)—The method of aspect 69 wherein delivering comprises delivering the device upstream of a bifurcation in the vessel.

Aspect (116)—The method of aspect 70 wherein delivering comprises delivering the device upstream of a bifurcation in the vessel.

Aspect (117)—The method of aspect 71 wherein delivering comprises delivering the device upstream of a bifurcation in the vessel.

Aspect (118)—The method of aspect 72 wherein delivering comprises delivering the device upstream of a bifurcation in the vessel.

Aspect (119)—The method of aspect 73 wherein delivering comprises delivering the device upstream of a bifurcation in the vessel.

Aspect (120)—The method of aspect 74 wherein delivering comprises delivering the device upstream of a bifurcation in the vessel.

Aspect (121)—The method of aspect 75 wherein delivering comprises delivering the device upstream of a bifurcation in the vessel.

Aspect (122)—The method of aspect 76 wherein delivering comprises delivering the device upstream of a bifurcation in the vessel.

Aspect (123)—The method of aspect 77 wherein delivering comprises delivering the device upstream of a bifurcation in the vessel.

Aspect (124)—The method of aspect 78 wherein delivering comprises delivering the device upstream of a bifurcation in the vessel.

Aspect (125)—The method of aspect 79 wherein delivering comprises delivering the device upstream of a bifurcation in the vessel.

Aspect (126)—The method of aspect 80 wherein delivering comprises delivering the device upstream of a bifurcation in the vessel.

Aspect (127)—The method of aspect 81 wherein delivering comprises delivering the device upstream of a bifurcation in the vessel.

Aspect (128)—The method of aspect 82 wherein delivering comprises delivering the device upstream of a bifurcation in the vessel.

Aspect (129)—The method of aspect 83 wherein delivering comprises delivering the device upstream of a bifurcation in the vessel.

Aspect (130)—The method of aspect 84 wherein delivering comprises delivering the device upstream of a bifurcation in the vessel.

Aspect (131)—The method of aspect 85 wherein delivering comprises delivering the device upstream of a bifurcation in the vessel.

Aspect (132)—The method of aspect 86 wherein delivering comprises delivering the device upstream of a bifurcation in the vessel.

Aspect (133)—The method of aspect 87 wherein delivering comprises delivering the device upstream of a bifurcation in the vessel.

Aspect (134)—The method of aspect 88 wherein delivering comprises delivering the device upstream of a bifurcation in the vessel.

Aspect (135)—The method of aspect 89 wherein delivering comprises delivering the device upstream of a bifurcation in the vessel.

Aspect (136)—The method of aspect 90 wherein delivering comprises delivering the device upstream of a bifurcation in the vessel.

Aspect (137)—The method of aspect 91 wherein delivering comprises delivering the device upstream of a bifurcation in the vessel.

Aspect (138)—The method of aspect 92 wherein delivering comprises delivering the device upstream of a bifurcation in the vessel.

While particular embodiments of the present invention have been shown and described, it will be obvious to those skilled in the art that changes and modifications can be made without departing from the embodiments of this invention in its broader aspects and, therefore, the appended claims are to encompass within their scope all such changes and modifications as fall within the true spirit and scope of the embodiments of this invention. Additionally, various embodiments have been described above. For convenience's sake, combinations of aspects composing invention embodiments have been listed in such a way that one of ordinary skill in the art may read them exclusive of each other when they are not necessarily intended to be exclusive. But a recitation of an aspect for one embodiment is meant to disclose its use in all embodiments in which that aspect can be incorporated without undue experimentation. In like manner, a recitation of an aspect as composing part of an embodiment is a tacit recognition that a supplementary embodiment exists that specifically excludes that aspect. All patents, test procedures, and other documents cited in this specification are fully incorporated by reference to the extent that this material is consistent with this specification and for all jurisdictions in which such incorporation is permitted.

Moreover, some embodiments recite ranges. When this is done, it is meant to disclose the ranges as a range, and to disclose each and every point within the range, including end points. For those embodiments that disclose a specific value or condition for an aspect, supplementary embodiments exist that are otherwise identical, but that specifically exclude the value or the conditions for the aspect.

What is claimed is:

1. A device comprising a catheter including:
a main body having a diffusion member delivery lumen through which a self-expandable diffusion member dimensioned for insertion within a blood vessel is advanced, the self-expandable diffusion member comprising a body, wherein the body comprises at least one fluid passage dimensioned to allow a blood flow within the vessel to flow through the body and create a region of turbulent blood flow within the blood vessel, and
a drug delivery lumen positioned upstream to the self-expandable diffusion member, and wherein the drug delivery lumen is positioned around the diffusion member delivery lumen and configured such that a drug delivered through the drug delivery lumen flows through the at least one fluid passage of the self-expandable diffusion member and mixes with the blood in the region of turbulent blood flow.

2. The device of claim 1 wherein the self-expandable diffusion member comprising a body comprises a pre-formed shape memory material.

3. The device of claim 2 wherein the pre-formed shape memory material comprises nitinol.

4. The device of claim 1 wherein the self-expandable diffusion member comprising a body comprises a net-like, braided structure.

5. The device of claim 4 wherein the net-like, braided structure comprises one, two, or more wires or filaments.

6. The device of claim 1 wherein the self-expandable diffusion member comprising a body comprises a donut structure.

7. The device of claim 6 wherein the donut structure comprises a substantially cylindrical body with a length, a largest diameter, and wherein the passage is coaxial to the cylindrical axis.

8. The device of claim 7 wherein the length ranges from one to ten times the largest diameter of the body.

9. The device of claim 8 wherein the body has a diameter of 50-105% of the vessel.

10. The device of claim 9 wherein the passage has a diameter that ranges from 15-80% of the largest diameter of the cylinder.

11. The device of claim 10 further comprising a connecting member that joins the main body to the expandable diffusion member comprising a body.

12. The device of claim 7 further comprising a connecting member that joins the main body to the expandable diffusion member comprising a body.

13. The device of claim 12 wherein the length ranges from one to ten times the largest diameter of the body.

14. The device of claim 13 wherein the body has a diameter of 50-105% of the vessel.

15. The device of claim 7 wherein the body has a diameter of 50-105% of the vessel.

16. The device of claim 7 wherein the passage has a diameter that ranges from 15-80% of the largest diameter of the cylinder.

17. The device of claim 1 wherein the self-expandable diffusion member has a body with a length wherein the length ranges from one to ten times the largest diameter of the body.

18. The device of claim 1 wherein the self-expandable diffusion member comprising a body further comprises a ball of wire or filament.

19. The device of claim 18 wherein the ball of wire or filament comprises a set of coplanar serpentine curves.

20. The device of claim 1 wherein the self-expandable diffusion member comprising a body further comprises an occlusion balloon.

* * * * *